United States Patent
Kim et al.

(10) Patent No.: US 10,263,339 B2
(45) Date of Patent: Apr. 16, 2019

(54) X-RAY DETECTOR AND X-RAY IMAGING APPARATUS HAVING THE SAME

(71) Applicant: SAMSUNG ELECTRONICS CO., LTD., Suwon-si (KR)

(72) Inventors: Jung Min Kim, Seoul (KR); Hoon Park, Seoul (KR); Il Seong, Yongin-si (KR); Woo Sung Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 103 days.

(21) Appl. No.: 15/216,858

(22) Filed: Jul. 22, 2016

(65) Prior Publication Data

US 2017/0025761 A1 Jan. 26, 2017

(30) Foreign Application Priority Data

Jul. 22, 2015 (KR) .................. 10-2015-0103825

(51) Int. Cl.
| | |
|---|---|
| *H01Q 9/04* | (2006.01) |
| *A61B 6/00* | (2006.01) |
| *H01Q 21/30* | (2006.01) |
| *H01Q 5/378* | (2015.01) |
| *H01Q 1/22* | (2006.01) |
| *H01Q 21/00* | (2006.01) |
| *H01Q 9/42* | (2006.01) |

(Continued)

(52) U.S. Cl.
CPC ......... *H01Q 9/0407* (2013.01); *A61B 6/4233* (2013.01); *A61B 6/4283* (2013.01); *A61B 6/4405* (2013.01); *A61B 6/4411* (2013.01); *A61B 6/4452* (2013.01); *A61B 6/56* (2013.01); *A61B 6/563* (2013.01); *H01Q 1/2291* (2013.01); *H01Q 5/378* (2015.01); *H01Q 9/0414* (2013.01); *H01Q 9/42* (2013.01); *H01Q 21/00* (2013.01); *H01Q 21/30* (2013.01); *G03B 42/02* (2013.01); *H01Q 1/36* (2013.01); *H01Q 5/392* (2015.01); *H01Q 21/28* (2013.01)

(58) Field of Classification Search
CPC .... H01Q 9/0407; H01Q 1/2291; H01Q 1/243; H01Q 1/24; H01Q 21/28; H01Q 21/00; H01Q 9/42; H01Q 5/378; H01Q 9/04; A61B 6/563; A61B 6/4411
USPC ................. 343/702, 700 MS; 250/370.11
See application file for complete search history.

(56) References Cited

U.S. PATENT DOCUMENTS 8,723,734 B2 * 5/2014 Chung .................. H01Q 1/243
343/700 MS
2001/0021643 A1 9/2001 Itoh
(Continued)

FOREIGN PATENT DOCUMENTS

JP 2006-94915 A 4/2006

OTHER PUBLICATIONS

Communication dated Sep. 25, 2017, from the European Patent Office in counterpart European Application No. 16179232.0.
(Continued)

*Primary Examiner* — Hai V Tran
(74) *Attorney, Agent, or Firm* — Sughrue Mion, PLLC

(57) ABSTRACT

The X-ray detector includes a side frame; a cover coupled to an outside of the side frame; a first antenna radiator supplied with a power by being coupled to the side frame; and a second antenna radiator provided in the cover while being spaced apart from the first antenna radiator, and configured to resonate with the first antenna radiator.

18 Claims, 38 Drawing Sheets

(51) Int. Cl.
   *G03B 42/02*    (2006.01)
   *H01Q 5/392*    (2015.01)
   *H01Q 1/36*     (2006.01)
   *H01Q 21/28*    (2006.01)

(56) References Cited

U.S. PATENT DOCUMENTS

| | | |
|---|---|---|
| 2011/0163937 A1 | 7/2011 | Jung et al. |
| 2011/0272588 A1* | 11/2011 | Jadrich ............... G01T 1/20 250/370.11 |
| 2012/0032859 A1 | 2/2012 | Lin |
| 2013/0099982 A1* | 4/2013 | Andrenko ........... H01Q 5/0072 343/700 MS |
| 2013/0135157 A1* | 5/2013 | Tsou ................... H01Q 1/2266 343/702 |
| 2013/0207854 A1* | 8/2013 | Ryu ..................... H01Q 5/35 343/702 |
| 2014/0180376 A1 | 6/2014 | Jennings |
| 2015/0255853 A1* | 9/2015 | Kwong ................ H01Q 1/44 343/702 |

OTHER PUBLICATIONS

Communication dated Nov. 25, 2016, issued by the European Patent Office in counterpart European Patent Application No. 16179232.0.
Communication dated May 9, 2018, issued by the European Patent Office in counterpart European Patent Application No. 16179232.0.
Communication dated Jan. 30, 2019, issued by the European Patent Office in counterpart European Application No. 18200571.0.

* cited by examiner

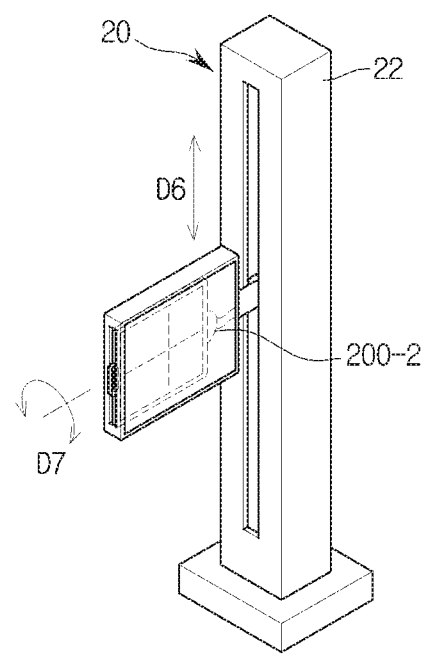

X-RAY DETECTOR AND X-RAY IMAGING APPARATUS HAVING THE SAME

CROSS-REFERENCE TO RELATED APPLICATION

This application claims priority from Korean Patent Application No. 10-2015-0103825, filed on Jul. 22, 2015 in the Korean Intellectual Property Office, the disclosure of which is incorporated herein by reference in its entirety.

BACKGROUND

1. Field

Exemplary embodiments relate to an X-ray detector and an X-ray imaging apparatus having the same, particularly an X-ray detector having a structure to improve a wireless communication performance, and an X-ray imaging apparatus having the same.

2. Description of Related Art

X-ray imaging apparatuses are devices that use X-radiation to obtain images of the inside of objects. The X-ray imaging apparatus images the inside of an object in a non-invasive method by irradiating X-rays to the object and detecting X-rays that have penetrated the object. Accordingly, a medical X-ray imaging apparatus may be used to diagnose injuries or diseases of the inside of an object, which may be hardly seen from the appearance of the object.

The detection of X-rays passed through the object is performed by an X-ray detector. The X-ray detector may transmit a data corresponding to the detected X-rays to the outside via a wired/wireless communication method.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments may provide an X-ray detector having an improved wireless communication performance and an X-ray imaging apparatus having the same.

In accordance with an aspect of an exemplary embodiment, an X-ray detector includes a side frame; a cover coupled to an outside of the side frame; a first antenna radiator fed with a power by being coupled to the side frame; and a second antenna radiator provided in the cover while being spaced apart from the first antenna radiator, and configured to resonate with the first antenna radiator.

The second antenna radiator may be disposed so that some portion thereof or all thereof is overlapped with the first antenna radiator.

The second antenna radiator may be disposed in an inner surface or an outer surface of the cover.

The second antenna radiator may be mounted to the cover.

The second antenna radiator may have a shape to resonate with the first antenna radiator.

The first antenna radiator may include a high frequency patch configured to radiate electromagnetic waves of a first frequency; and a low frequency patch configured to radiate electromagnetic waves of a second frequency.

The second antenna radiator may be disposed in a position that is overlapped with a high frequency patch.

The first frequency may be WiFi communication frequency and the second frequency may be Bluetooth communication frequency.

The X-ray detector may further include a connection member configured to connect the high frequency patch to the low frequency patch, electrically.

The X-ray detector may further include a power supply configured to feed electromagnetic waves energy to the first antenna radiator.

The second antenna radiator may be indirectly fed with a power through the first antenna radiator.

In accordance with an aspect of an exemplary embodiment, an X-ray imaging apparatus includes an X-ray detector provided with a first antenna radiator for a wireless communication; and an accommodation portion configured to accommodate the X-ray detector and provided with a second antenna radiator configured to resonate with the first antenna radiator.

The second antenna radiator may be disposed so that some portion thereof or all thereof is overlapped with the first antenna radiator.

The second antenna radiator may be indirectly fed with a power through the first antenna radiator.

The first antenna radiator may include a high frequency patch configured to radiate electromagnetic waves of a first frequency; and a low frequency patch configured to radiate electromagnetic waves of a second frequency.

The first frequency may be WiFi communication frequency and the second frequency may be Bluetooth communication frequency.

The X-ray detector may include a plurality of the first antenna radiators to communicate with the outside by Multiple Input Multiple Output (MIMO) method.

BRIEF DESCRIPTION OF THE DRAWINGS

The above and/or other aspects will become more apparent by describing certain exemplary embodiments with reference to the accompanying drawings, in which:

FIGS. 6A and 6B are views illustrating an example of method for mounting an X-ray detector of an X-ray imaging apparatus to a scanning stand in accordance with an exemplary embodiment;

DETAILED DESCRIPTION

Figure 1:
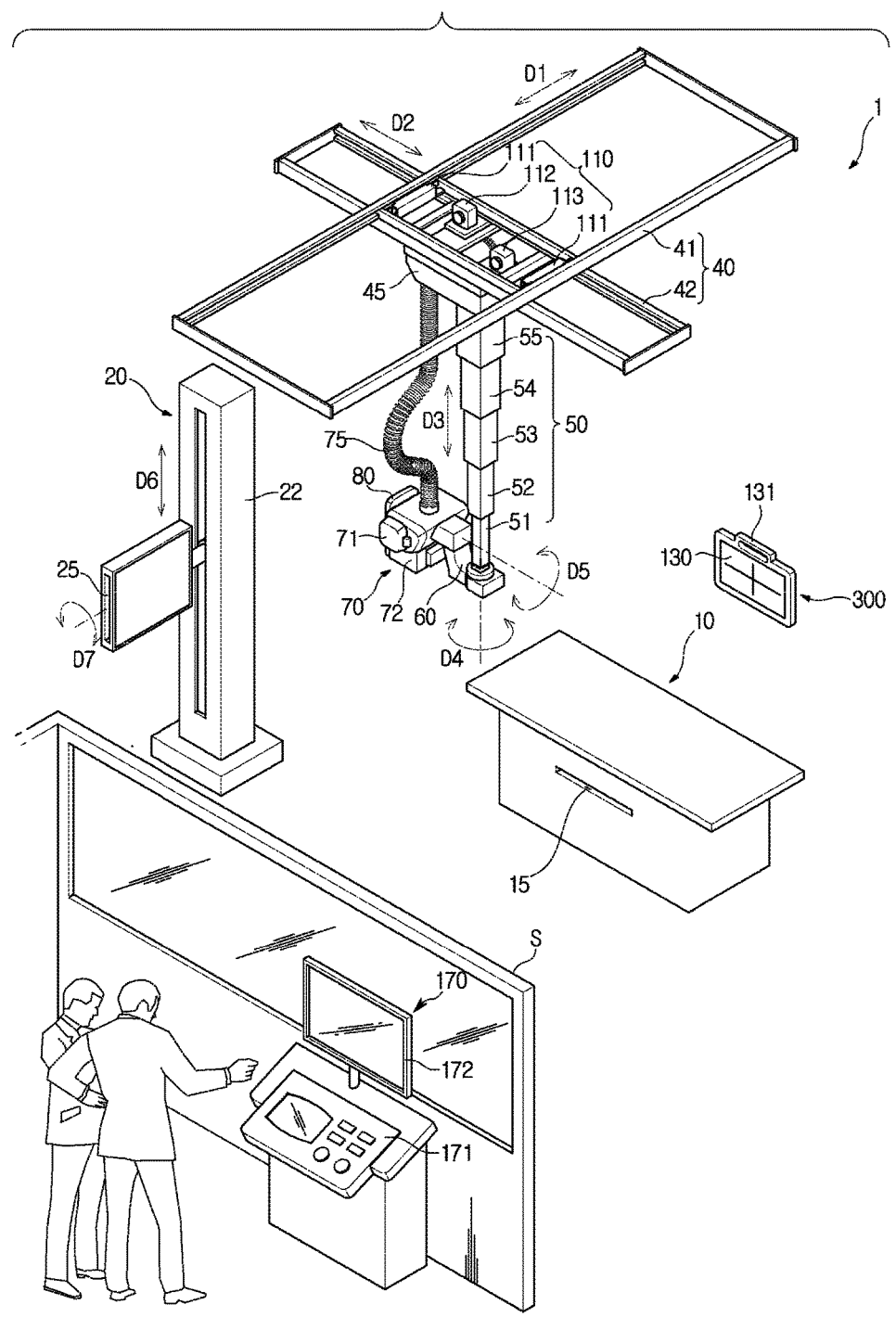
FIG. 1 is a perspective view illustrating an X-ray imaging apparatus in accordance with an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

In the following detailed description, the terms of "front end", "rear end", "upper portion", "lower portion", "upper end", "lower end" and the like may be defined by the drawings, but the shape and the location of the component is not limited by the term.

Figure 2:
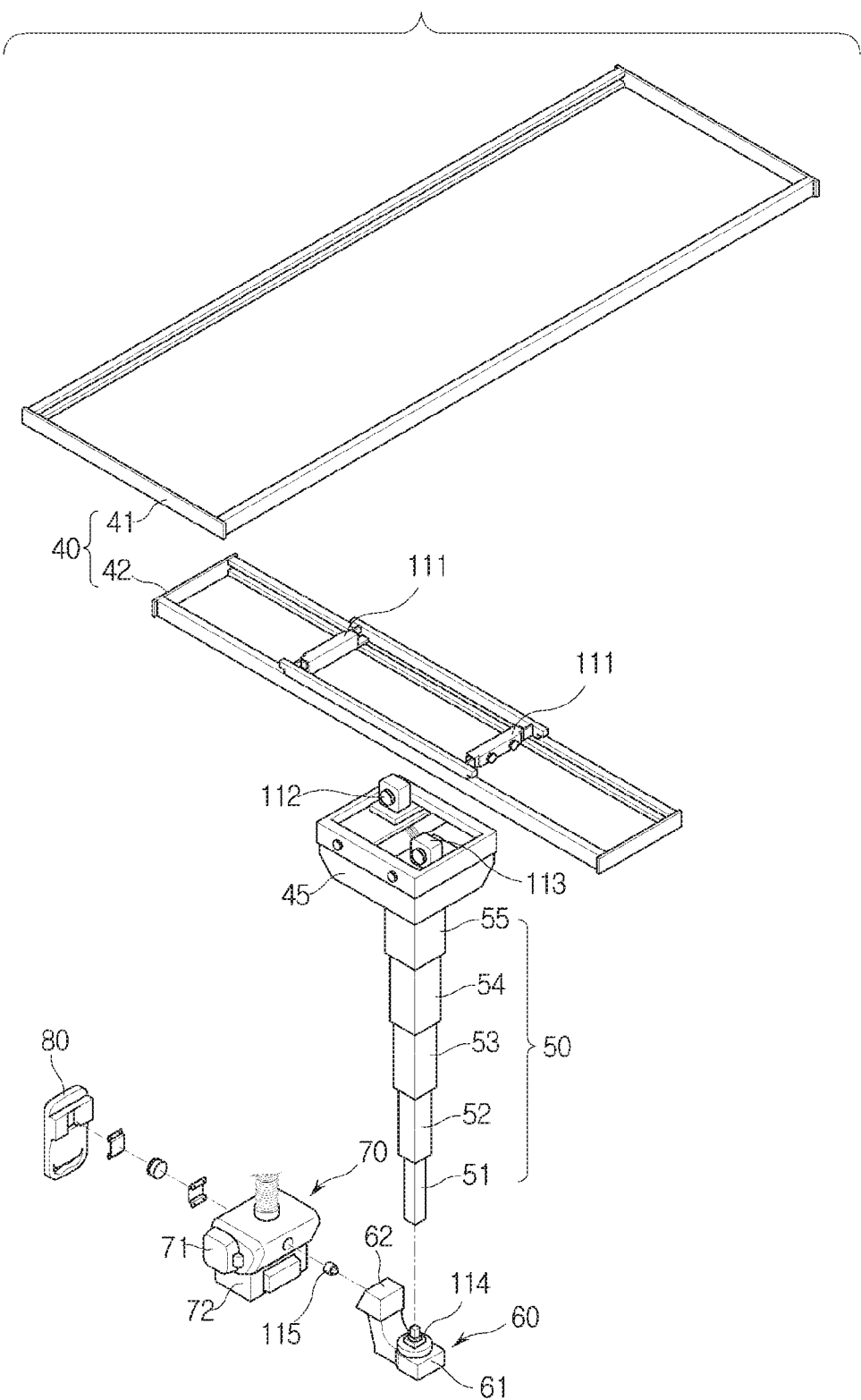
FIG. 2 is an exploded-perspective view of an X-ray imaging apparatus in accordance with an exemplary embodiment.
Figure 3:
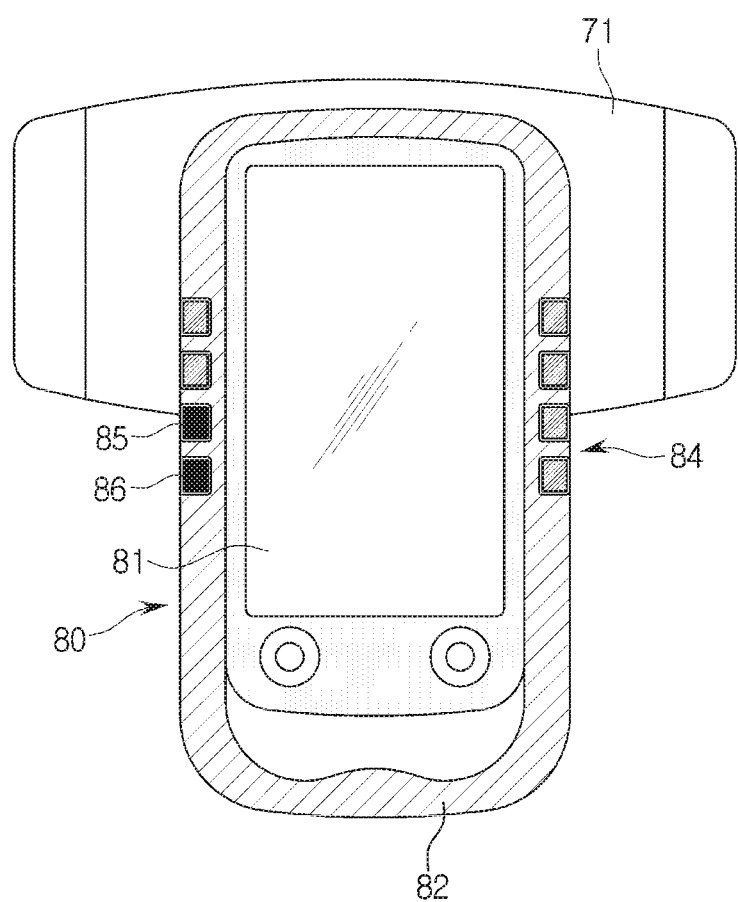
FIG. 3 is a front view illustrating an operation controller of an X-ray imaging apparatus in accordance with an exemplary embodiment.

FIG. 1 is a perspective view illustrating an X-ray imaging apparatus in accordance with an exemplary embodiment, FIG. 2 is an exploded-perspective view of an X-ray imaging apparatus in accordance with an exemplary embodiment, and FIG. 3 is a front view illustrating an operation controller of an X-ray imaging apparatus in accordance with an exemplary embodiment.

As illustrated in FIGS. 1 to 3, an X-ray imaging apparatus 1 may include a guide rail 40, a moving carriage 45, a post frame 50, a motor 110, an X-ray source 70, X-ray detector 300, an operation controller 80, and a workstation 170. The X-ray imaging apparatus 1 may further include a scanning table 10 to which the X-ray detector 300 is mounted, and a scanning stand 20.

The guide rail 40, the moving carriage 45, and the post frame 50 may serve to move the X-ray source 70 toward an object.

The guide rail 40 may have a first guide rail 14 and a second guide rail 42 installed to form a predetermined angle between them. The first and second guide rails 41 and 42 may extend each other at right angles.

The first guide rail 41 may be installed on the ceiling of an examination room where the X-ray imaging apparatus 1 is placed.

The second guide rail 42 may be located below the first guide rail 41 and mounted to the first guide rail 41 in a slide manner. The first guide rail 41 may have a roller (not shown) movable along the first guide rail 41. The second guide rail 42 may be connected to the roller (not shown) and movable along the first guide rail 41.

A first direction D1 is defined as a direction in which the first guide rail 41 extends, and a second direction D2 is defined as a direction in which the second guide rail 42 extends. Therefore, the first and second directions D1 and D2 may be perpendicular to each other and parallel to the ceiling of the examination room.

The moving carriage 45 may be located below the second guide rail 42 so that the moving carriage 45 may be moved along the second guide rail 42. The moving carriage 45 may have a roller (not shown) to be movable along the second guide rail 42. Accordingly, the moving carriage 45 may be movable with the second guide rail 42 in the first direction D1 and movable along the second guide rail 42 in the second direction D2. The post frame 50 may be located below the moving carriage 45 while being fixed to the moving carriage 45. The post frame 50 may include a plurality of posts 51, 52, 53, 54, and 55.

The plurality of posts 51, 52, 53, 54, and 55 may be insertably coupled to each other. The length of the post frame 50 may increase or decrease in up or down direction in the examination room while being fixed to the moving carriage 45.

A third direction D3 is defined as the direction in which the post frame 50 increases or decreases. Thus, the third direction D3 is perpendicular to the first and second directions D1 and D2.

The X-ray source 70 is a device for irradiating X-rays to an object. The object may be a living body of a human or animal, but is not limited thereto. Any object whose internal structure is imaged by the X-ray imaging apparatus 1 may be an object.

The operation controller 80 configured to provide a user interface may be provided in one side of the X-ray source 70. A user may be a person who performs diagnosis of the object by using the X-ray imaging apparatus 1, and may include a medical staff such as a doctor, a radiological technologist and a nurse, but is not limited thereto. Anyone who uses the X-ray imaging apparatus 1 may be a user.

As illustrated in FIG. 3, the operation controller 80 may include a first display 81 and a button 84 so that a user may be allowed to input information related to X-ray scanning or operate a variety of devices. The first display 81 may be implemented by Cathode Ray Tube (CRT), Liquid Crystal Display (LCD), and Light Emitting Diode (LED), but is not limited thereto.

The button 84 may include a rotation selection button 84 manipulated when the user wants to rotate the X-ray source 70 in a fourth direction D4 or a fifth direction D5. That is, when the user wants to rotate the X-ray source 70 in the fourth direction D4, the user may rotate the X-ray source 70 in the fourth direction D4 after pressing a fourth direction rotation selection button 85, and when the user wants to rotate the X-ray source 70 in the fifth direction D5, the user may rotate the X-ray source 70 in the fifth direction D5 after pressing a fifth direction rotation selection button 86, or may rotate the X-ray source 70 in the fifth direction D5 while pressing the fifth direction rotation selection button 86. Positions of the rotation selection button 84 illustrated in FIG. 3 are just examples, and the rotation selection button 84 may be disposed in different positions.

The operation controller 80 may include a handle 82 that the user may grasp. The user may grasp the handle 82 of the operation controller 80 and may apply a force or torque to the X-ray source 70 so as to move the X-ray source 70. This is defined as a manual movement mode. The movement of the X-ray source 70 may be controlled by a motor controller (not shown), and this is defined as an automatic movement mode. In FIG. 3, the handle 82 is disposed at a lower portion of the operation controller 80. However, this is just an example, and the handle 82 may also be disposed in a different position of the operation controller 80.

Particularly, the X-ray source 70 may include an X-ray tube 71 generating X-rays, and a collimator 72 guiding the generated X-rays to the object.

Figure 4:
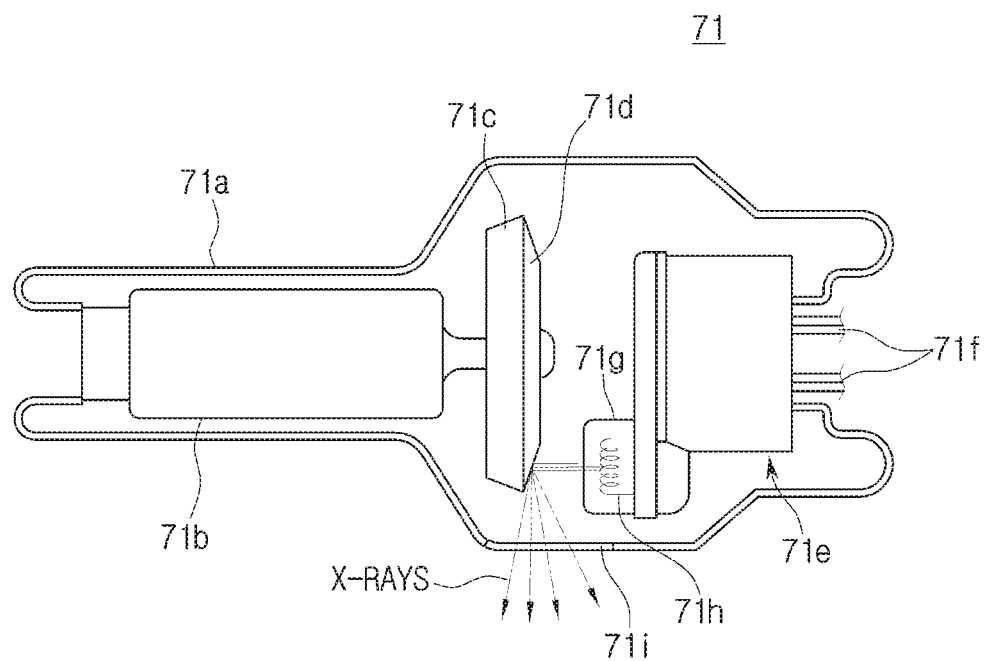
FIG. 4 is a cross-sectional view illustrating an internal structure of an X-ray tube of an X-ray imaging apparatus in accordance with an exemplary embodiment.

FIG. 4 is a cross-sectional view illustrating an internal structure of an X-ray tube of an X-ray imaging apparatus in accordance with an exemplary embodiment.

Referring to FIG. 4, the X-ray tube 71 may be implemented as a bipolar vacuum tube that includes positive and negative electrodes 71*c* and 71*e*, and the body of the vacuum tube may be a glass tube 71*a* made of e.g., hard silicon glass.

The negative electrode 71*e* may include a filament 71*h* and a focusing electrode 71*g* that focuses electrons, the focusing electrode 71*g* being also called a focusing cup. Thermions are generated by making the inside of the glass tube 71*a* in a high vacuum state of about 10 mmHg and heating the filament 71*h* of the negative electrode 71*e* to a high temperature. As an example of the filament 71*h*, a tungsten filament may be used, which may be heated by applying a current to an electric wire 71*f* coupled with the filament 71*h*. However, the embodiment is not limited to the occasion where the negative electrode 71*e* employs the filament 71*h*, and it is also possible to have a carbon nano-tube for the negative electrode 71*e*, which may be driven by high-rate pulses.

The positive electrode 71*c* is mainly formed of copper, and a target material 71*d* is applied or disposed on the side that faces the negative electrode 71*e*, the target material may include a high resistive material, such as Cr, Fe, Co, Ni, W, Mo, or the like. The higher the melting point of the target material is, the smaller the focal spot size is.

When a high voltage is applied across the negative and positive electrodes 71*e* and 71*c*, thermions are accelerated and collide with the target material 71*d* of the positive electrode thereby generating X-rays. The X-ray may be irradiated out through the window 71*i* that is formed of a thin film of Beryllium.

The target material 71*d* may be rotated by a rotor 71*b*. While the target material 71*d* is rotating, the heat accumulation rate may increase more than ten times per unit area in comparison with an occasion where the target material 71*d* is stationary, and the focal spot size may decrease.

A voltage applied across the negative and positive electrodes 71*e* and 71*c* of the X-ray tube 71 is called a tube voltage whose magnitude may be represented by a crest value kVp. As the tube voltage increases, the speed of the thermion increases and as a result, energy of X-radiation (energy of photon radiation) from collision of the thermion with the target material increases. Current flowing through the X-ray tube 71 is called tube current, which may be represented by an average value mA. As the tube current increases, the amount of X-rays (the number of photons) increases. That is, the energy of X-radiation may be controlled by the tube voltage and the amount of X-rays may be controlled by the tube current.

Referring to FIGS. 1 and 2 again, a rotating joint 60 may be arranged between the X-ray source 70 and the post frame 50.

The rotating joint 60 may connect the X-ray source 70 to the post frame 50 and may support the weight applied to the X-ray source 70.

The rotating joint 60 may include a first rotating joint 61 connected to a lower post 51 of the post frame 50 and a second rotating joint 62 connected to the X-ray source 70.

The first rotating joint 61 may be arranged to be rotatable with respect to the central axis of the post frame 50 that extends in the up/down direction in the examination room. Accordingly, the first rotating joint 61 may rotate on the plane perpendicular to the third direction D3. The rotation direction of the first rotating joint 61 may be newly defined as a fourth direction D4 corresponding to a rotation direction of the axis parallel to the third direction D3.

The second rotating joint 62 may be arranged to be rotatable on the plane perpendicular to the ceiling of the examination room. Accordingly, the second rotating joint 62 may rotate in the rotation direction of the axis parallel to the first direction D1 or the second direction D2. The rotation direction of the second rotating joint 62 may be newly defined as a fifth direction D5 corresponding to the rotation direction of the axis that extends in the first or second direction D1 or D2. The X-ray source 70 may be coupled with the rotating joint 60 and rotatably moved in the fourth or fifth direction D4 or D5. In addition, the X-ray source 70 may be coupled with the post frame 50 by the rotating joint 60 and straightly moved in the first, second, or third direction D1, D2, or D3.

To move the X-ray source 70 in any of the first to fifth directions D1 to D5, the motor 110 may be provided. The motor 110 may be electric motors driven electrically, and may include an encoder.

The motor 110 may include a first motor 111, a second motor 112, a third motor 113, a fourth motor 114, and a fifth motor that correspond to the first to fifth directions D1 to D5, respectively.

The motors 110 may be arranged in various positions in consideration with the convenience of design. For example, the first motor 111 moving the second guide rail 42 in the first direction D1 may be arranged around the first guide rail 41; the second motor 112 moving the moving carriage 45 in the second direction D2 may be arranged around the second guide rail 42; and the third motor 113 increasing or decreasing the length of the post frame 50 in the third direction D3 may be arranged inside of the moving carriage 45. Furthermore, the fourth motor 114 rotatably moving the X-ray source 70 in the fourth direction D4 may be arranged around the first rotating joint 61, and the fifth motor 115 rotatably moving the X-ray source 70 in the fifth direction D5 may be arranged around the second rotating joint 62.

Each of the motors 110 may be coupled with a power delivery device (not shown) to move the X-ray source 70 straightly or rotatably in any of the first to fifth directions D1 to D5. The power delivery device (not shown) may be a commonly-used belt and pulley, chain and sprocket, shaft, etc.

The workstation 170 may include an input receiver 171 and a second display 172 and may provide a user interface via the second display 172. Thus, the user may input a variety of information regarding X-ray imaging or may operate devices by using the workstation 170. In addition, the user may input various commands related to an operation of the X-ray imaging apparatus 1 using the workstation 170, for example, commands to select an image scanning position or commands to start X-ray imaging. Also, the user may check an image that is acquired when X-ray imaging is performed using the workstation 170.

The input receiver 171 may include at least one of a switch, a keyboard, a track ball, a mouse, and a touch screen. When the input receiver 171 may be implemented by a graphical user interface (GUI), such as a touch screen, i.e., software, the input receiver 171 may be displayed on the second display 172. The second display 172 may be a CRT, an LCD or an organic LED, like in the first display 81, but is not limited thereto.

Also, various processing units, such as a central processing unit (CPU) or a graphic processing unit (GPU), and a printed circuit board (PCB) may be built in the workstation 170, and various kinds of storing units may also be built in the workstation 170 as needed.

Therefore, a main component of the X-ray imaging apparatus 1, e. g., a control unit (not shown) may be disposed in the workstation 170 so that various determinations for the operation of the x-ray imaging apparatus 1 may be performed, or various control signals may be generated.

Particularly, the workstation 170 may control the X-ray source 70 to emit X-rays to the object, generate an X-ray imaging regarding the object based on a data received from the X-ray detector 300, and display the generated X-ray imaging via the second display 172.

The workstation 170 having the above configuration may be disposed in a separate independent space (S) in which the X-rays are blocked. The workstation 170 may be connected to the X-ray source 70 and the X-ray detector 300 through wired communication or wireless communication.

The X-ray detector 300 is a device configured to detect X-rays passed through the object. An incidence surface 130 on which the X-rays are incident, may be provided on a front surface of the X-ray detector 300, and a detection panel 120 may be disposed in the X-ray detector 300. A plurality of pixels responding to the X-rays may be arranged on the detection panel 120 to have a matrix shape. A handle 131 may be disposed in the center of a top end of the X-ray detector 300 so that the use ve or carry the X-ray detector 300.

The X-ray detector 300 may be operated in various imaging modes according to its position when performing X-ray imaging. Particularly, the X-ray detector 300 may be operated in a table mode in which the X-ray detector 300 is mounted on the image scanning table 10, or in a stand mode in which the X-ray detector 300 is mounted on the image scanning stand 20, or may not be mounted on the image scanning table 10 or image scanning stand 20 but may be operated in a portable mode in which the X-ray detector 300 is disposed in an arbitrary position according to the position of the object and a part to be imaged of the object. Particularly, accommodation portions 15 and 25 may be disposed in the image scanning table 10 and the image scanning stand 20, respectively, so that the X-ray detector 300 may be mounted on the image scanning table 10 or image scanning stand 20. An accommodation portion disposed in the image scanning table 10 may be defined as a first accommodation portion 15, and an accommodation portion disposed in the image scanning stand 20 may be defined as a second accommodation portion 25. The second accommodation portion 25 may be disposed to be movable in a longitudinal direction of a support 22 and to be rotated in a rotation direction of an axis perpendicular to the longitudinal direction of the support 22, as illustrated in FIG. 1. In this case, the longitudinal direction of the support 22 may be defined as a sixth direction D6, and the rotation direction of an axis perpendicular to the sixth direction D6 may be defined as a seventh direction D7.

The X-ray detector 300 may be a device configured to detect incident X-rays, and may detect X-rays passed through the object.

The detectionX-rays may be performed by the detection panel 120 inside the X-ray detector 300. The detection panel 120 may convert the detected X-ray into an electric signal, to obtain an X-ray image of the inside of the object.

The detection panel 120 may be classified based on a material composition method, a method for converting the detected X-ray into an electric signal and a method for obtaining an electric signal.

The detection panel 120 may be divided into a case where it is formed of a single element and a case where it is formed of composite elements, based on the material composition method.

In the case where the detection panel 120 is formed of a single material, a section that detects the X-ray and generates an electric signal and a section that reads and processes the electric signal may be formed of a semiconductor of a single material or may be manufactured with a single process. For example, photo detectors e.g. a Charge Coupled Device (CCD) or a Complementary Metal Oxide Semiconductor (CMOS) may be used in a single manner.

In the case the detection panel 120 is formed of composite elements, a section that detects the X-ray and generates an electric signal and a section that reads and processes the electric signal may be formed of different materials or manufactured with different processes. For example, there may be an occasion where photo detectors, e.g., photo diodes, CCD, CdZnTe, etc., are used to detect an X-ray and CMOS Read Out Integrated Circuits (ROICs) are used to read and process the electric signal; an occasion where strip detectors are used to detect an X-ray and the CMOS ROICs are used to read and process the electric signal; an occasion where a-Si or a-Se flat panel systems are used, and so on.

The detection panel 120 may be divided into direct conversion scheme and indirect conversion scheme based on the method for converting the X-ray to an electric signal.

In the direct conversion scheme, when X-rays are irradiated, a pair of electron and hole is generated temporarily inside the photo detector and electric potential across both electrodes of the photo detector causes the electron to be moved to the positive electrode and the hole to be moved to the negative electrode. The detection panel 120 may convert the movements into an electric signal. In the direct conversion scheme, a material used for the photo detector may be a-Se, CdZnTe, HgI2, PbI2, etc.

In the indirect conversion scheme, the X-ray irradiated from the X-ray source 70 reacts with a scintillator to cause photons having a visible wavelength in a visible spectrum to be emitted, and the photo detector detects the photons and converts them to an electric signal. The material used for the photo detector in the indirect conversion scheme may be e.g., a-Si, and the scintillator may be GADOX scintillator in the form of a thin film, or a micro column type or needle structure type CSI (T1).

The detection panel 120 may be divided into a charge integration mode for storing charges for a certain period of time and obtaining a signal from the charges, and a photon counting mode for counting the number whenever a signal is generated by a single X-ray photon, based on the method for obtaining the electric signal.

The detection panel 120 may employ any of the aforementioned schemes.

Figure 5A:
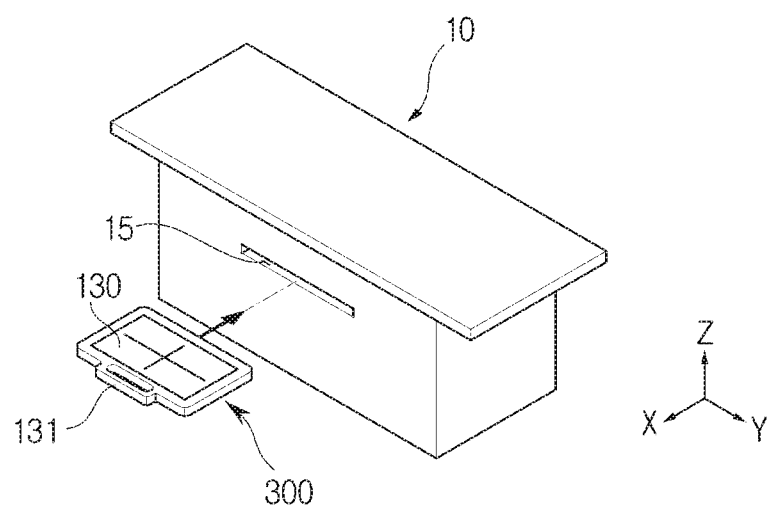
FIGS. 5A and 5B are views illustrating an example of method for mounting an X-ray detector of an X-ray imaging apparatus to a scanning table in accordance with an exemplary embodiment.
Figure 5B:
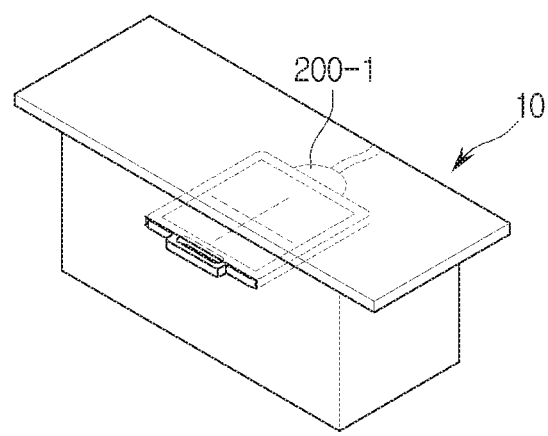

As mentioned above, the X-ray detector 300 may be operated in the table mode, the stand mode, and the portable mode to detect X-rays. Hereinafter the position of the X-ray detector 300 in each mode will be described with reference to FIGS. 5 to 7. FIGS. 5A and 5B are views illustrating an example of method for mounting an X-ray detector of an X-ray imaging apparatus to a scanning table in accordance with an exemplary embodiment, FIGS. 6A and 6B are views illustrating an example of method for mounting an X-ray detector of an X-ray imaging apparatus to a scanning stand in accordance with an exemplary embodiment, and FIG. 7 is a view illustrating an example in which an X-ray detector of an X-ray imaging apparatus is in a portable mode in accordance with an exemplary embodiment.

The connection module 200 may be provided in plural to correspond to each scanning mode. As illustrated in FIGS. 5 to 7, the connection module 200 may include a table connection module 200-1 corresponding to the table mode, a stand connection module 200-2 corresponding to the stand mode, and a portable connection module 200-3 corresponding to the portable mode. The position and the number of the connection module 200 is an example, and thus another example in which only the table connection module 200-1 and the stand module 200-2 may be provided or in which four and more connection modules may be provided may be allowed. However, according to an embodiment, the connection module 200 may include the table connection module 200-1, the stand connection module 200-2, and the portable connection module 200-3.

As illustrated in FIGS. 5A and 5B, the table connection module 200-1 may be provided in the first accommodation portion 15. When scanning the object lying on the scanning table 10, the X-ray detector 300 may be inserted into the first accommodation portion 15 provided in the scanning table 10 so that the X-ray detector 300 may be mounted to the scanning table 10. When being inserted into the first accommodation portion 15, the X-ray detector 300 may be in a state of being parallel to a bottom surface, that is a plane surface formed by a X-axis and a Y-axis, as illustrated in FIG. 5A. After being inserted into the first accommodation portion 15, the X-ray detector 300 may be kept in the state of being parallel to a bottom surface, that is a plane surface formed by the X-axis and the Y-axis, as illustrated in FIG. 5B. Meanwhile, the X-ray detector 300 inserted into the first accommodation portion 15 may be coupled to the table connection module 200-1, and a case in which the X-ray detector 300 is inserted into the first accommodation portion 15 and then coupled to the table connection module 200-1 may represent the table mode.

Figure 6A:
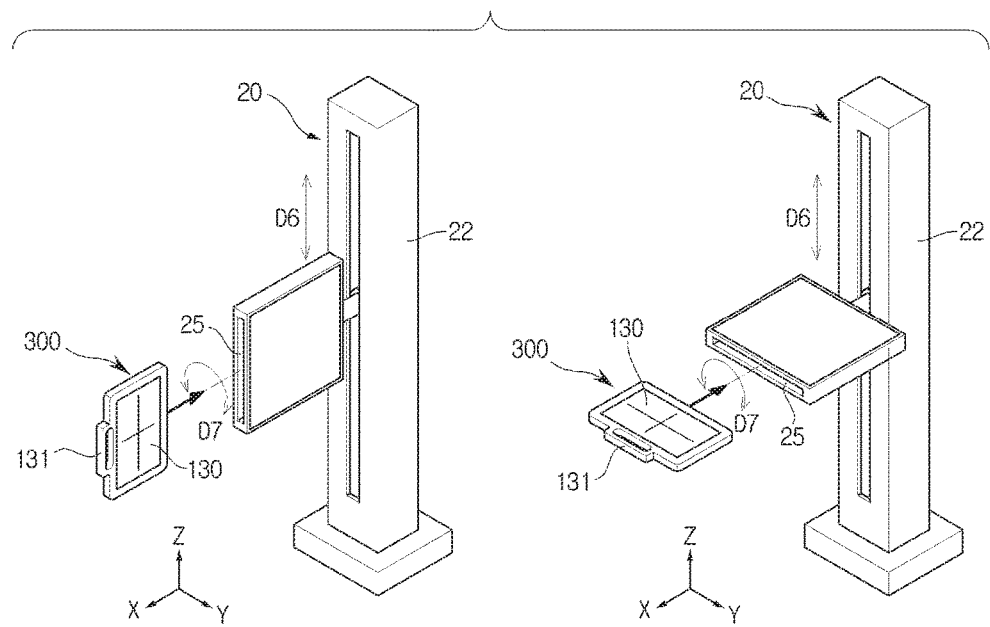
Figure 7:
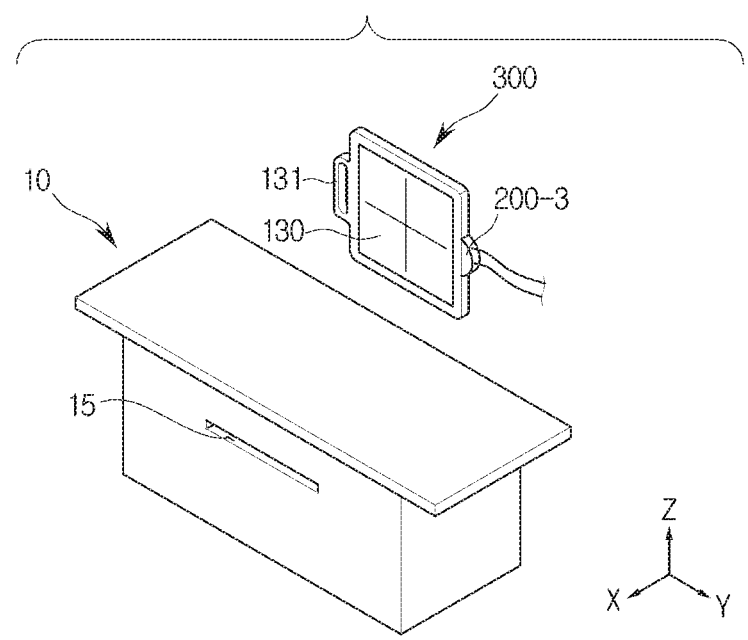
FIG. 7 is a view illustrating an example in which an X-ray detector of an X-ray imaging apparatus is in a portable mode in accordance with an exemplary embodiment.

As illustrated in FIGS. 6A and 6B, the stand connec dole 200-2 may be provided in the second accommodation portion 25. When scanning the object standing by the scanning stand 20, the X-ray detector 300 may be inserted into the second accommodation portion 25 provided in the scanning stand 20 so that the X-ray detector 300 may be mounted to the scanning stand 20. Since the second accommodation portion 25 is rotatable in the seventh direction (D7), when being inserted into the second accommodation portion 25, the X-ray detector 300 may be in a state of being perpendicular to a bottom surface, that is a plane surface formed by the X-axis and a Z-axis, as illustrated in the left side of FIG. 6A, or in a state of being parallel to a bottom surface, that is a plane surface formed by a X-axis and a Y-axis, as illustrated in the right side FIG. 6A. After being inserted into the second accommodation portion 25, the X-ray detector 300 may be kept in the state of being perpendicular to a bottom surface, that is a plane surface formed by the X-axis and the Z-axis, due to the rotation of the second accommodation portion 25, as illustrated in FIG. 6B. Meanwhile, the X-ray detector 300 inserted into the second accommodation portion 25 may be coupled to the stand connection module 200-2, and a case in which the X-ray detector 300 is inserted into the second accommodation portion 25 and then coupled to the stand connection module 200-2 may represent the stand mode.

When scanning moving object as well as lying or standing object, the X-ray detector 300 may be in a portable state without being mounted to the scanning table 10 or the scanning stand 20, and it may represent a portable mode. As illustrated in FIG. 7, in the portable mode, the X-ray detector 300 may be coupled to the portable connection module 200-3 and the portable connection module 200-3 may be placed in an arbitrary position that allows the scanning to be performed easily in the portable mode. For example, the portable connection module 200-3 may be placed in a rear surface of an upper panel of the scanning table 10, as illustrated in FIG. 7.

FIGS. 8A to 10 are views illustrating examples of a position according to a table connection module, a stand connection module and a portable connection module in an X-ray imaging apparatus in accordance with an exemplary embodiment.

Figure 8A:
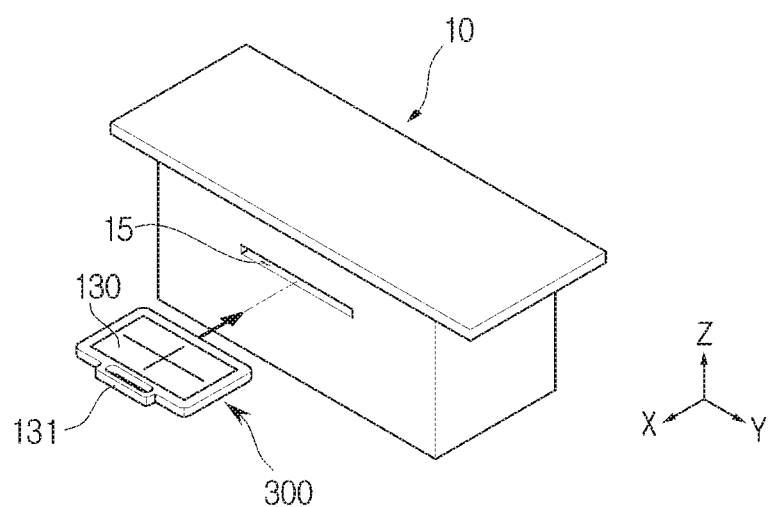
FIGS. 8A and 8B are views illustrating an example of a position according to a table connection module, a stand connection module and a portable connection module in an X-ray imaging apparatus in accordance with an exemplary embodiment.
Figure 8B:
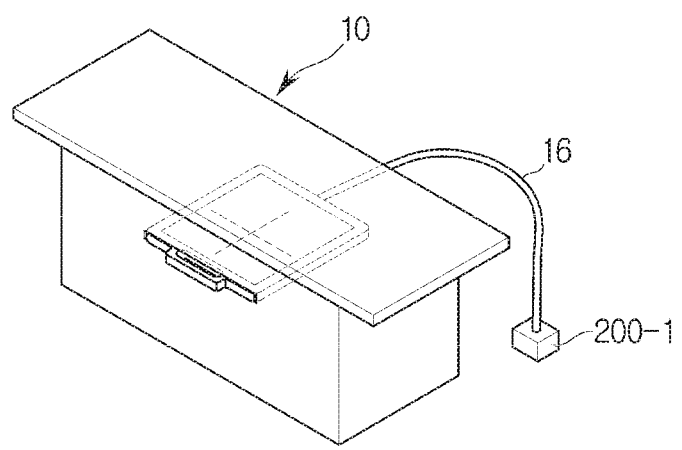

As illustrated in FIGS. 8A and 8B, the table connection module 200-1 may be provided in the outside of the first accommodation portion 15, and may be coupled to the X-ray detector 300, which is inserted into the first accommodation portion 15, via a cable 36. For this, the table connection module 200-1 may be placed adjacent to the scanning table 10.

Figure 9A:
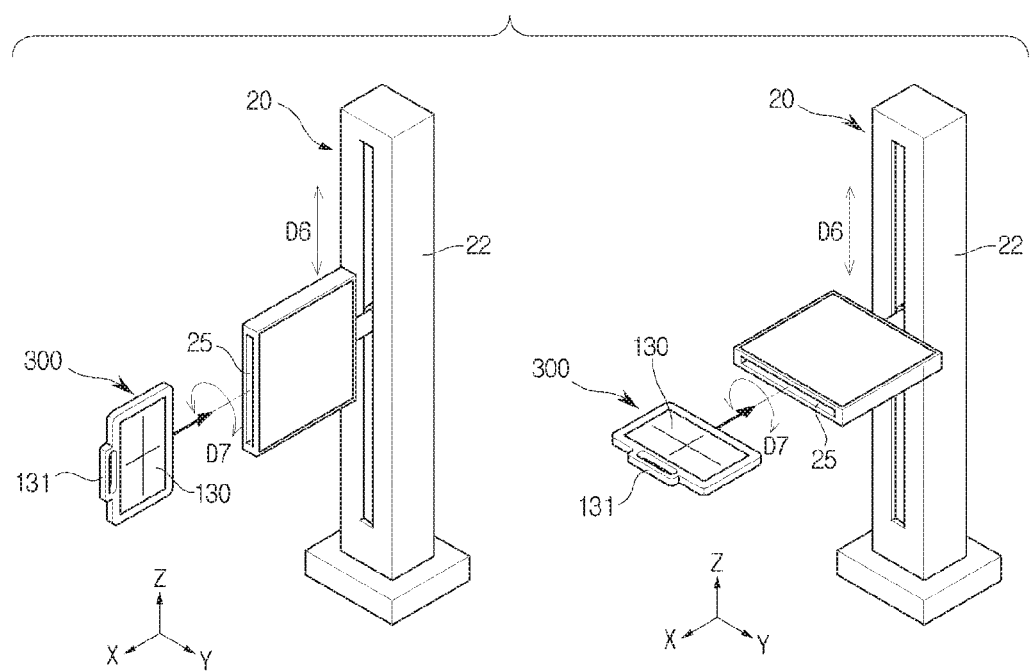
FIGS. 9A and 9B are views illustrating an example of a position according to a table connection module, a stand connection module and a portable connection module in an X-ray imaging apparatus in accordance with an exemplary embodiment.
Figure 9B:
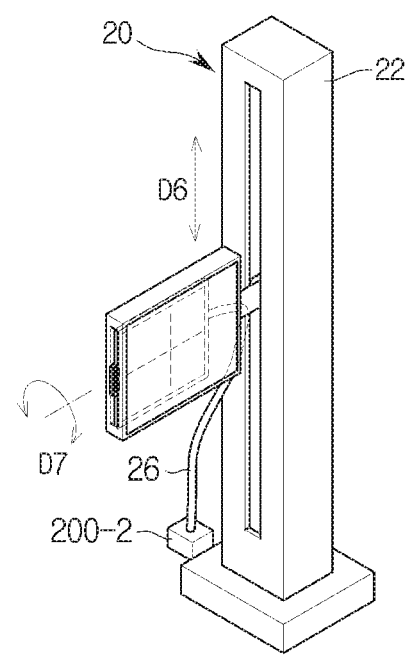

As illustrated in FIGS. 9A and 9B, the stand connection module 200-2 may be provided in the outside of the second accommodation portion 25, and may be coupled to the X-ray detector 300, which is inserted into the second accommodation portion 25, via the cable 36. For this, the stand connection module 200-2 may be placed adjacent to the scanning stand 20.

Figure 10:
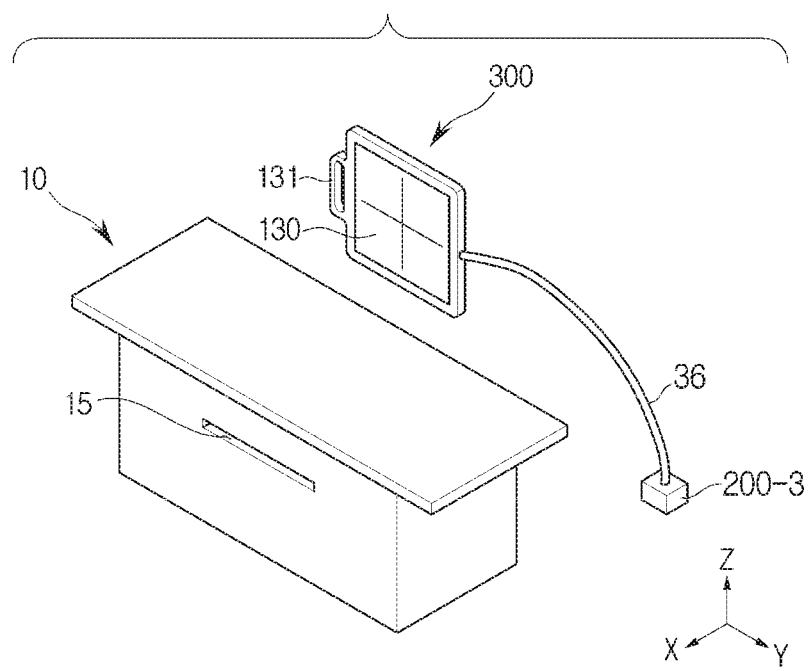
FIG. 10 is a view illustrating an example of a position according to a table connection module, a stand connection module and a portable connection module in an X-ray imaging apparatus in accordance with an exemplary embodiment.

As illustrated in FIG. 10, the portable connection module 200-3 may be coupled to the X-ray detector 300 in the portable mode, via the cable 36.

Meanwhile, when the X-ray detector 300 receives power via a wire and coupled to the workstation via the wire, the connection module 200 may play a role of connecting the X-ray detector 300 to an external power supply device and a network hub. Aside from the configuration of connecting the external power supply device, the network hub, and the X-ray detector 300, it may be implemented by a board to which an electric element is mounted.

At first, a case where the connection module 200 includes a configuration to connect the external power supply device, the network hub, and the X-ray detector 300 will be described as an example. In this case, the connection module 200 may represent power box. However, the connection module 200 may be defined by a configuration and operation thereof, but not defined by its name.

The X-ray detector 300 may wirelessly communicate with the workstation 170. Hereinafter, the structure of the X-ray detector 300 will be described in detail.

Figure 11:
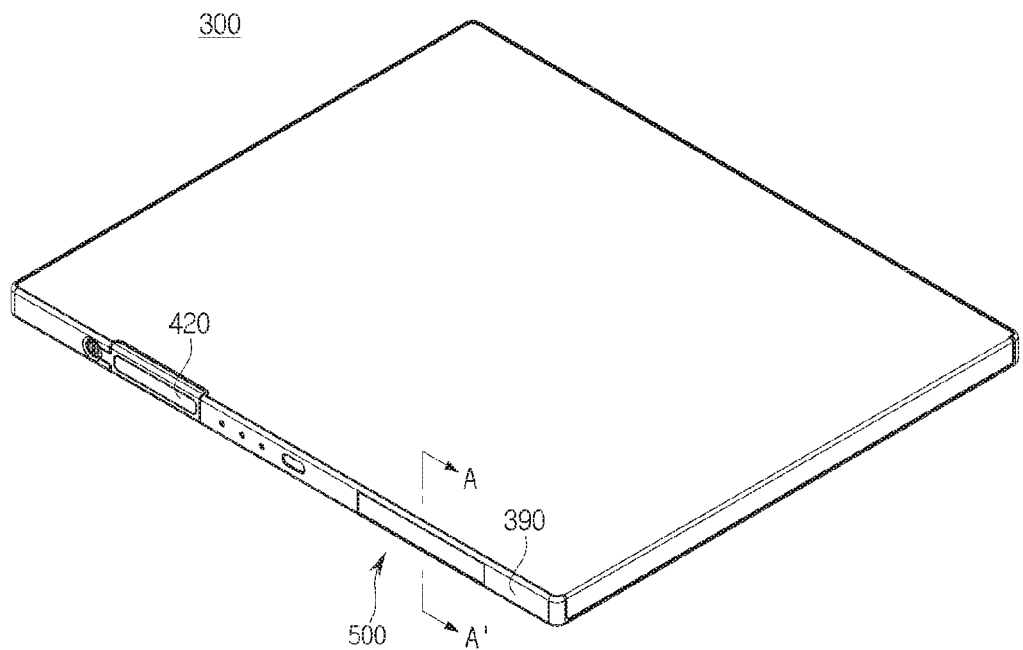
FIG. 11 is a perspective view illustrating an X-ray detector of an X-ray imaging apparatus in accordance with an exemplary embodiment.
Figure 12:
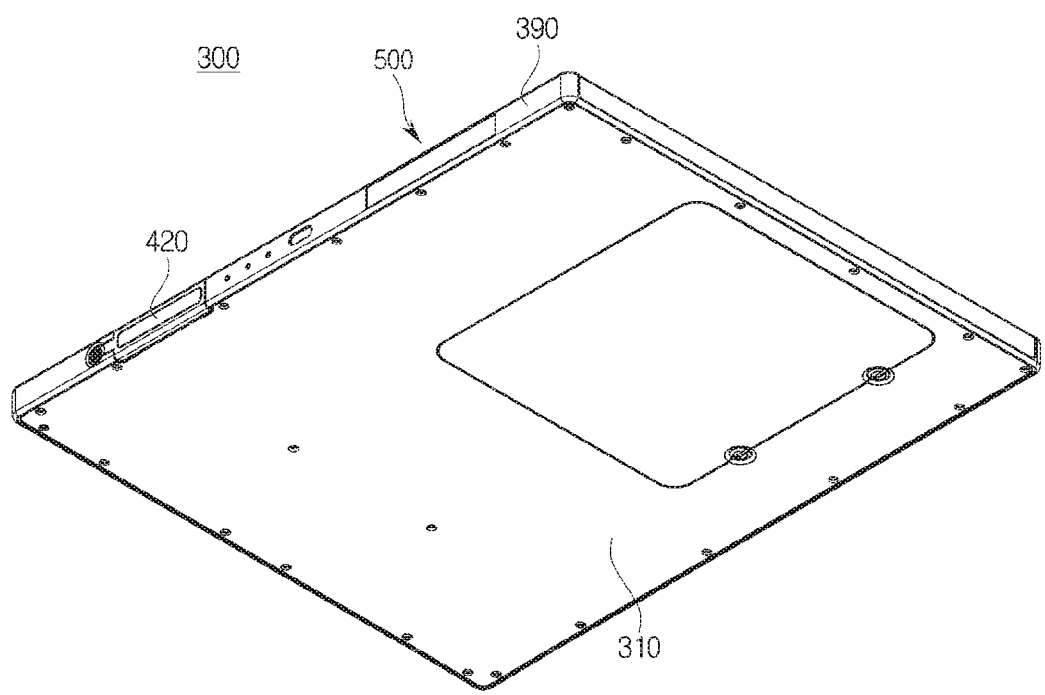
FIG. 12 is a perspective view illustrating a bottom of an X-ray detector of an X-ray imaging apparatus in accordance with an exemplary embodiment.
Figure 13:
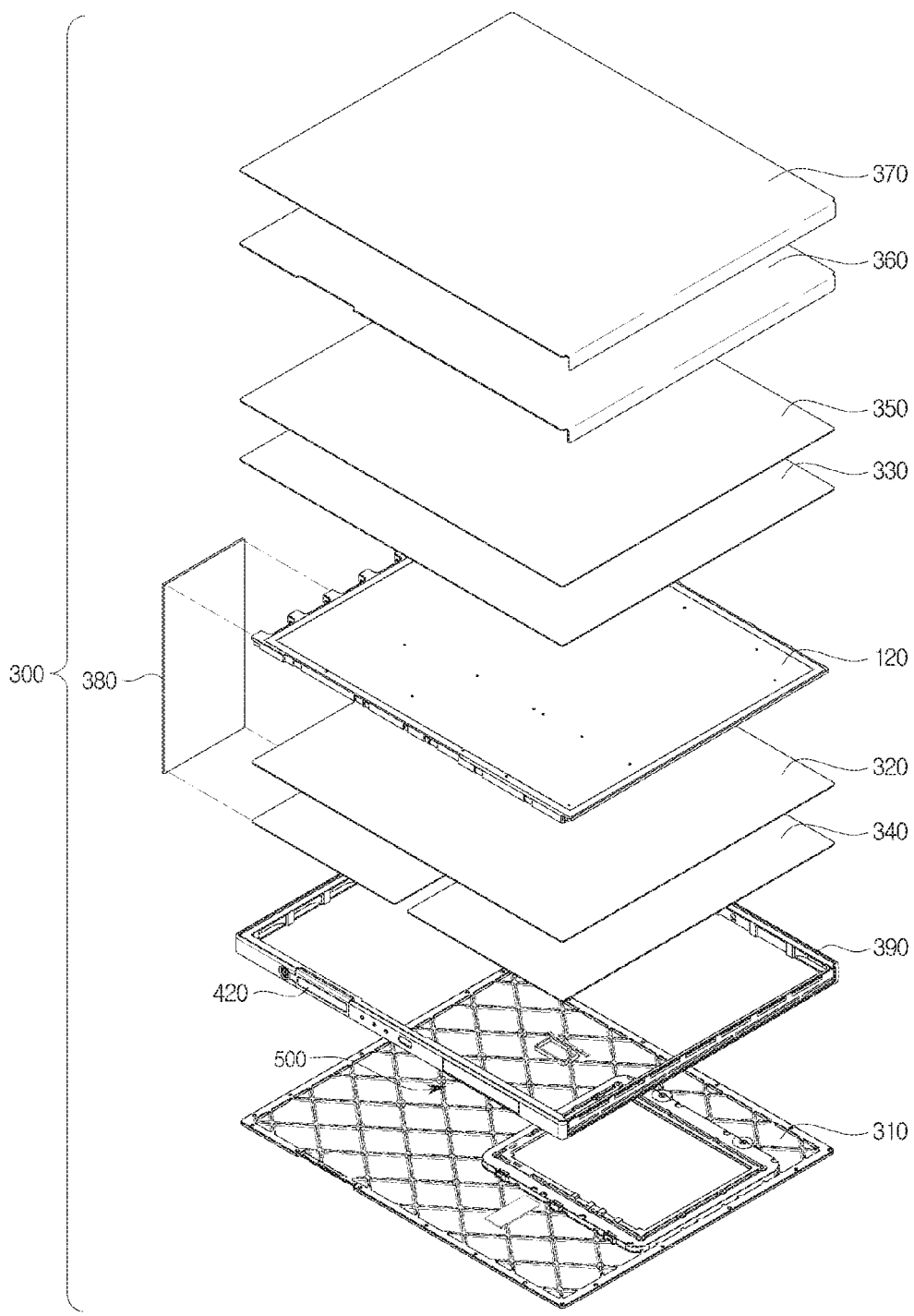
FIG. 13 is an exploded-perspective view illustrating an X-ray detector of an X-ray imaging apparatus in accordance with an exemplary embodiment.

FIG. 11 is a perspective view illustrating an X-ray detector of an X-ray imaging apparatus in accordance with an exemplary embodiment, FIG. 12 is a perspective view illustrating a bottom of an X-ray detector of an X-ray imaging apparatus in accordance with an exemplary embodiment, and FIG. 13 is an exploded-perspective view illustrating an X-ray detector of an X-ray imaging apparatus in accordance with an exemplary embodiment. Hereinafter foreign material may include dust, blood, and liquid.

As illustrated in FIGS. 11 to 13, the X-ray detector 300 may be configured to detect X-rays emitted from the X-ray source 70.

The X-ray detector 300 may include a top frame 360, a lateral member 390, and a bottom frame 310, all of which forms an exterior of the X-ray detector 300 by coupling to each other.

The top frame 360 may form an upper exterior of the X-ray detector 300. The top frame 360 may be provided in the form of carbon plate. A deco sheet 370 may be further provided in one surface of the top frame 360.

The bottom frame 310 may form a lower exterior of the X-ray detector 300. The bottom frame 310 may be formed of the same material as the top frame 360.

The lateral member 390 may form a lateral exterior of the X-ray detector 300. The top frame 360 may be coupled to one side of the lateral member 390, and the bottom frame 310 may be provided in the other side of the lateral member 390. Meanwhile, the lateral member 390 may be integrally formed with at least one of the top frame 360 and the bottom frame 310.

In the lateral member 390, a terminal for a wired communication and a communication assembly for a wireless communication may be provided. The terminal and the communication assembly will be described later in detail.

An accommodation space in which a device is placed may be formed by the bottom frame 310, the lateral member 390 and the top frame 360. In the inside of the accommodation space, an insulating substrate 320, a detection panel 120, a scintillator 330, and a circuit board 340 may be placed. The insulating substrate 320, the detection panel 120, the scintillator 330, and the circuit board 340 may be protected from an external impact by the top frame 360, the lateral member 390, and the bottom frame 310.

The insulating substrate 320 may support the detection panel 120 and the scintillator 330. The detection panel 120 may be mounted to one surface of the insulating substrate 320, and the scintillator 330 may be mounted to the detection panel 120. The circuit board 340 may be placed on the other side of the insulating substrate 320.

The scintillator 330 may include phosphor. The scintillator 330 may convert incident X-rays into visible rays. A cover 350 may be provided in one side of the scintillator 330 to protect the scintillator 330. The cover 350 may be formed of metal material, e.g. aluminum. The cover 350 may be placed on a lower side of the top frame 360.

The plurality of pixels may be provided in the detection panel 120, and a photoelectric conversion element, e.g. a thin film transistor and a photo diode may be provided in the plurality of pixels. The detection panel 120 may read out the intensity of the light passed through the scintillator 330 by pixel unit. An electrical circuit may be provided in the detection panel 120 to transmit the output of the photoelectric conversion element to the outside.

The circuit board 340 may perform the calculation to obtain an imaging regarding an object by using data that is obtained based on a signal that is read-out by the detection panel 120. The circuit board 340 may include a memory and a calculation unit. The memory may store shadow information of an object according to radiation angle of X-rays and the calculation unit may calculate a radiation angle of X-ray based on the shadow shape of the object formed on the detection panel 120 and the shadow information of the memory. The memory and the calculation unit may be placed in the outside of the X-ray detector 300.

The detection panel 120 and the circuit board 340 may be connected via a flexible printed circuit board (PCB) 380. In the flexible PCB 380, a read-out terminal (not shown) configured to read out information of the detection panel 120 may be provided.

Figure 14:
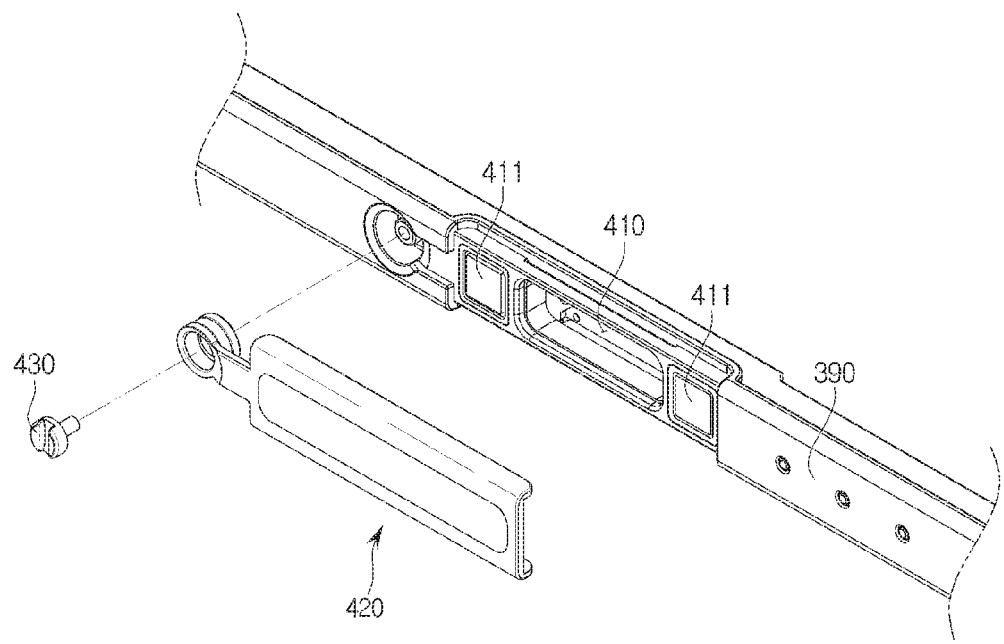
FIG. 14 is an exploded-perspective view illustrating a cap of an X-ray imaging apparatus in accordance with an exemplary embodiment.

FIG. 14 is an exploded-perspective view illustrating a cap of an X-ray imaging apparatus in accordance with an exemplary embodiment.

Referring to FIG. 14, the X-ray detector 300 may further include a terminal 410 for the wired communication.

The terminal 410 may be formed one side of the lateral member 390. The terminal 410 may have magnetic properties. Therefore, the connection module 200 may be coupled to the terminal 410 due to the magnetic properties. Particularly, a magnetic substance (not shown) having an opposite polarity to the terminal 410 may be provided in the connection module 200 so that the connection module 200 may be coupled to the terminal 410.

A cap 420 may be placed to be a position corresponding to the terminal 410 so that foreign materials may be prevented from being introduced to the terminal 410 to which the connection module 200 is coupled. The cap 420 may be coupled to the lateral member 390 to open/close the terminal 410 to which the connection module 200 is coupled.

At least one end portion of the cap 420 may be fixedly coupled to the lateral member 390. For example, one end portion of the cap 420 may be fixedly coupled to the lateral member 390 by a fixation member 430, e.g. a bolt. The cap 420 may be rotated with respect to the fixation member 430 as an axis while an end portion of the cap 420 is fixed to the lateral member 390.

The cap 420 may be coupled to the terminal 410 by using magnetic properties. For this, the cap 420 may include metal member, e.g. stain steel. The cap 420 may interact with at least one magnetic substance 411 provided around the terminal 410 by the metal member.

The X-ray detector 300 may further include a communication assembly or assemblies 500 for the wireless communication. Hereinafter, the communication assembly 500 provided in the X-ray detector 300 will be described in detail.

Figure 15A:
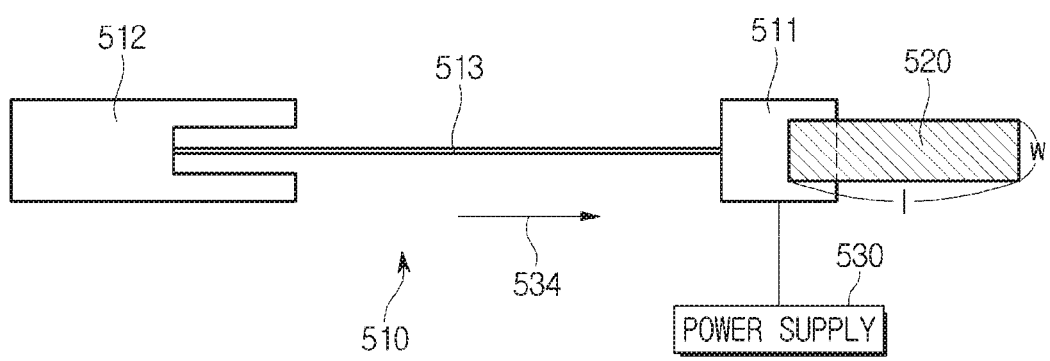
FIGS. 15A and 15B schematically illustrate a communication assembly in accordance with an exemplary embodiment.
Figure 15B:
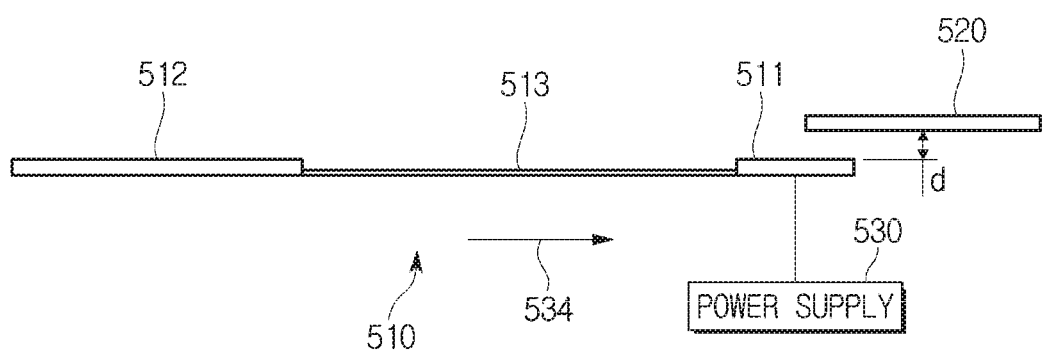

FIGS. 15A and 15B schematically illustrate a communication assembly in accordance with an exemplary embodiment, and FIGS. 16A, 16B, 16C, 16D, 16E, 16F, 16G, and 16H are views illustrating various patterns of a second antenna radiator. Particularly, FIG. 15A is a plan view illustrating an arrangement of the antenna radiator, and FIG. 15B is a cross-sectional view illustrating an arrangement of the antenna radiator.

Referring to FIGS. 15A and 15B, the communication assembly 500 may include a plurality antenna radiators 510 and 520, a power supply 530. Particularly, the communication assembly 500 may include a first antenna radiator 510 and a second antenna radiator 520.

The power supply 530 may feed, i.e., transmit, electromagnetic energy to the first antenna radiator 510 and a second antenna radiator 520. The power supply 530 may be provided in the circuit board 340 and may feed a power to at least one of the first antenna radiator 510 and a second antenna radiator 520. An antenna radiator receiving an electromagnetic energy by the power supply 530 may transmit a desired signal to the outside by radiating an electromagnetic wave according to the electromagnetic energy.

Particularly, the power supply 530 may be electrically connected to the first antenna radiator 510 via an electrical connection device, e.g. conductive tape, C-Clip, Pogo-Pin, or soldering, but is not limited thereto. For example, the power supply 530 may be placed apart from the first antenna radiator 510 with a certain distance and may indirectly feed a power to the first antenna radiator 510.

The first antenna radiator 510 may radiate an electromagnetic signal. Particularly, the first antenna radiator 510 may receive an electromagnetic energy from the power supply 530 and may radiate an electromagnetic energy based on the supplied electromagnetic energy, to the outside.

As illustrated in FIGS. 15A and 15B, the first antenna radiator 510 may be fed with the power from the power supply 530 by being electrically connected to the power supply 530, but the power feed method of the first antenna radiator 510 is not limited thereto.

The first antenna radiator 510 may be formed in the form of a thin film having a certain pattern. The pattern of the first antenna radiator 510 may be determined by an operating frequency band of the first antenna radiator 510.

The first antenna radiator 510 may have a plurality of operating frequency bands. For this, the first antenna radiator 510 may include a plurality of patches having various operating frequency bands.

Particularly, the first antenna radiator 510 may include a high frequency patch 511 configured to radiate an electromagnetic wave of a first frequency and a low frequency patch 512 configured to radiate an electromagnetic wave of a second frequency. In this case, the shape and the patter of the high frequency patch 511 and the low frequency patch 512 may be determined by each operating frequency.

For example, the high frequency patch 511 may have WiFi communication radiation pattern operated in 5 GHz band, and the low frequency patch 512 may have Bluetooth communication radiation pattern operated in 2.4 GHz band.

The low frequency patch 512 and the high frequency patch 511 may be electrically connected via a connection member 513. The connection member 513 may be formed of conductive material to electrically connect the low frequency patch 512 to the high frequency patch 511. Accordingly, a microstrip line of the high frequency patch 511 and the low frequency patch 512 may be formed by the connection member 513.

That is, the low frequency patch 512 may be fed with power through the high frequency patch 511, but the power feed method of the low frequency patch 512 is not limited thereto. Therefore, the low frequency patch 512 may be fed with power by using a variety of power feed methods.

The second antenna radiator 520 may improve the radiation performance of the first antenna radiator 510 by resonating with the first antenna radiator 510. That is, the second antenna radiator 520 may be electrically coupled to the first antenna radiator 510 by the resonance of the first antenna radiator 510.

In addition, the second antenna radiator 520 may be configured by a patch in the form of a thin film having a certain pattern. The pattern of the second antenna radiator 520 may be determined by a resonance frequency band. At this time, the resonance frequency band of the second antenna radiator 520 may be determined by the operating frequency of the first antenna radiator 510.

As illustrated in FIG. 15A, the second antenna radiator 520 may be implemented by a square patch having a certain length (l) and a certain width (w). For example, the second antenna radiator 520 may be implemented by a patch having a length of 10~20 mm and a width of 2~6 mm, but the shape of the second antenna radiator 520 is not limited thereto.

Figure 16A:
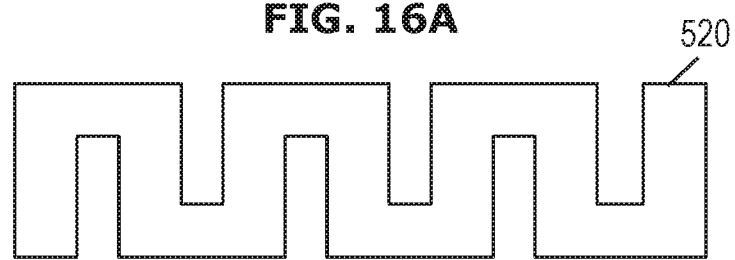
FIGS. 16A, 16B, 16C, 16D, 16E, 16F, 16G, and 16H are views illustrating various patterns of a second antenna radiator.
Figure 16B:
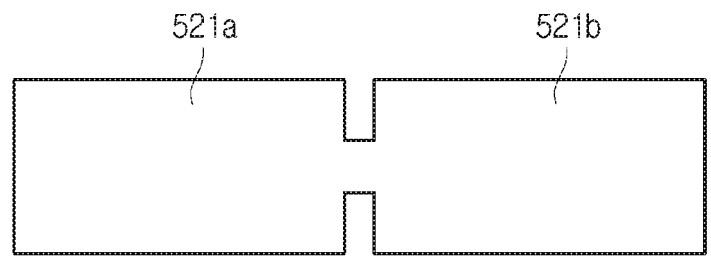
Figure 16C:
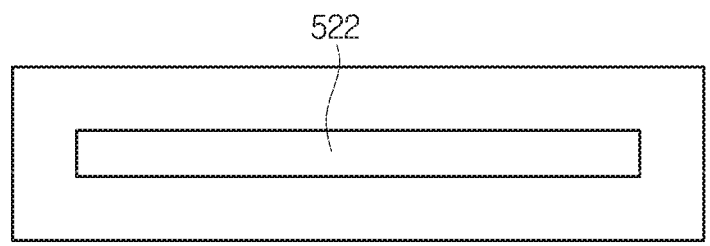
Figure 16D:
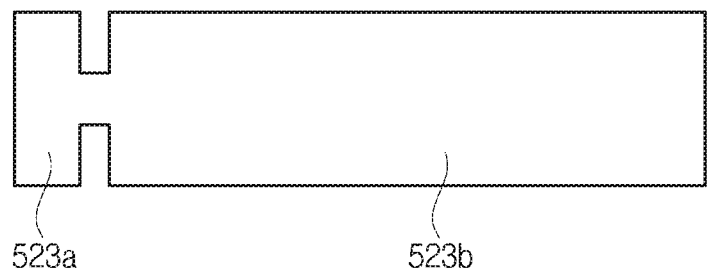
Figure 16E:
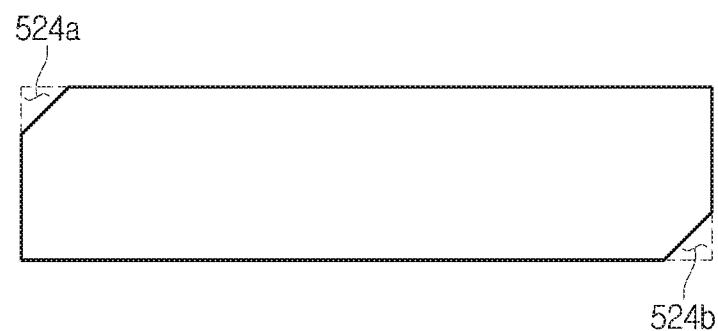
Figure 16F:
Figure 16G:

For example, the second antenna radiator 520 may have a meander line shape, as illustrated in FIG. 16A, a symmetrical shape in which the same size square patches 521a and 521b are connected, as illustrated in FIG. 16B, a slot shape in which an opening 522 is formed in the center of the patch, as illustrated in FIG. 16C, an symmetrical shape in which two square patch 523a and 523b, both of which have different size from each other, are connected, as illustrated in FIG. 16D, a truncate shape in which at least one corner 524a and 524b of the square patch is cut, as illustrated in FIG. 16E, a shape having a curved edge, illustrated in FIG. 16F, and a slit shape having a slit 525, illustrated in FIG. 16G.

Figure 16H:
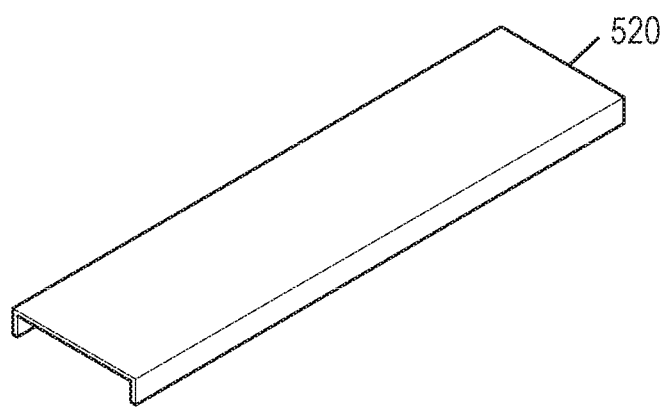

In addition, as neeeded, the second antenna radiator 520 may be provided in a three dimensional shape, illustrated in FIG. 16H or in the form of the symbol of manufacturer of the X-ray detector 300.

There may be no limitation in the power feed method of the second antenna radiator 520, but the second antenna radiator 520 may be indirectly fed with power through the first antenna radiator 510. For this, the second antenna radiator 520 may be provided apart from the first antenna radiator 510 with a certain distance (d), as illustrated in FIG. 15B, and for the indirect feed power, at least one portion of the second antenna radiator 520 may be overlapped with the first antenna radiator 510 with respect to a longitudinal direction 534 of the communication assembly 500 that coincides with a lengthwise dimension of the first antenna radiator 510, as illustrated in FIG. 15A.

For example, the second antenna radiator 520 may be disposed apart from the high frequency patch 511 of the first antenna radiator 510 with a distance of from 0.5 mm to 3 mm, and at least one portion of the second antenna radiator 520 may be disposed to be overlapped with the high frequency patch 511 of the first antenna radiator 510. Accordingly, the second antenna radiator 520 may be indirectly fed with power through the high frequency patch 511.

As mentioned above, when the second antenna radiator 520 is indirectly fed with power through the high frequency patch 511, the second antenna radiator 520 may resonate with the high frequency patch 511 and may improve the radiation performance regarding the first frequency band.

The aforementioned communication assembly 500 may be provided in one side of the X-ray detector 300. Hereinafter an arrangement structure of the communication assembly 500 will be described with reference to the drawings.

Figure 17:
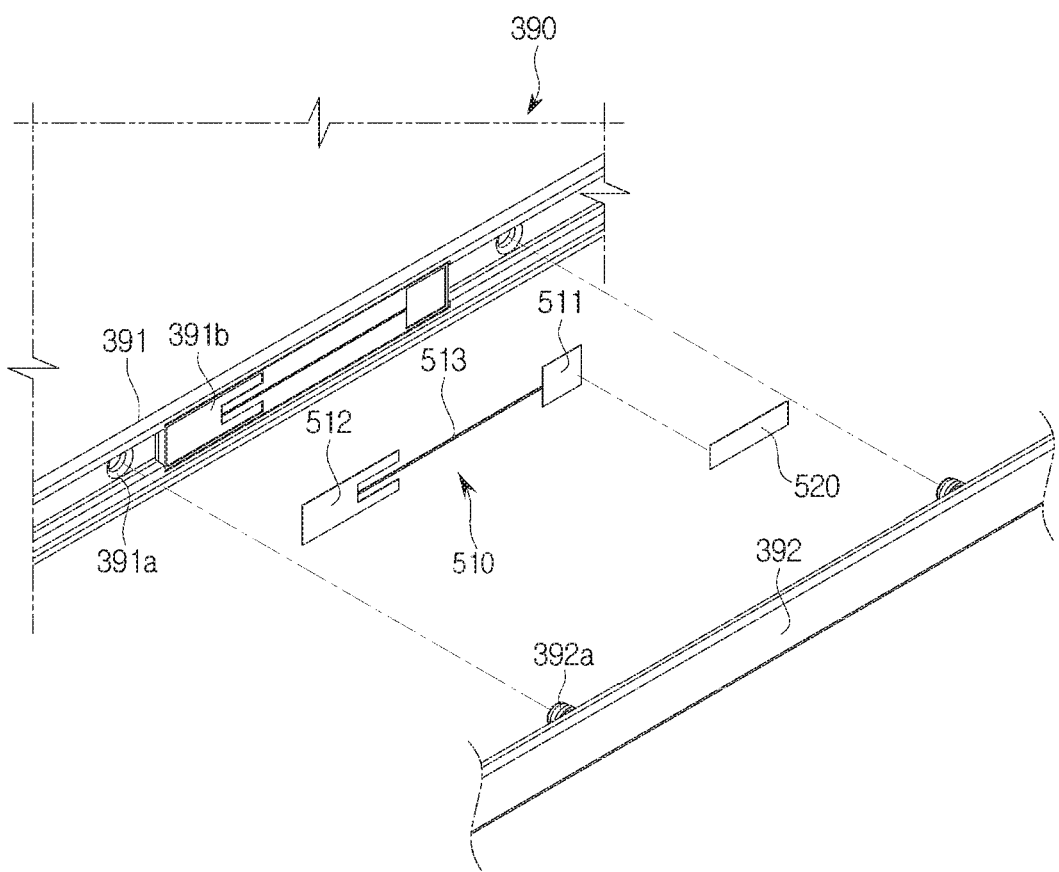
FIG. 17 is an exploded-perspective view illustrating a communication assembly of an X-ray detector in accordance with an exemplary embodiment.

FIG. 17 is an exploded-perspective view illustrating a communication assembly of an X-ray detector in accordance with an exemplary embodiment.

Figure 18:
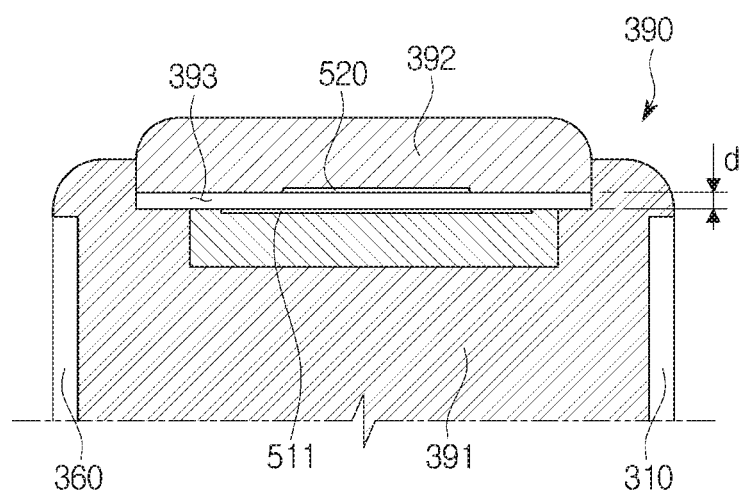
FIG. 18 is a cross-sectional view taken along line A-A' of an X-ray detector of FIG. 13 to illustrate a communication assembly of an X-ray detector in accordance with an exemplary embodiment.
Figure 19A:
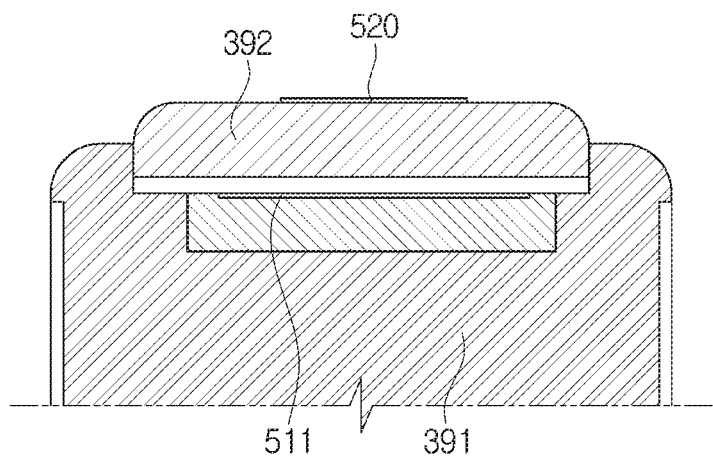
FIGS. 19A 19B, 19C, and 19D are cross-sectional views illustrating various positions of antenna radiator.
Figure 19B:
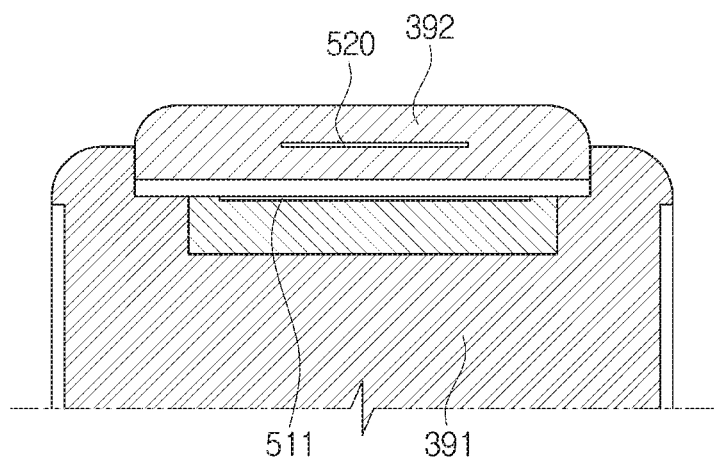
Figure 19C:
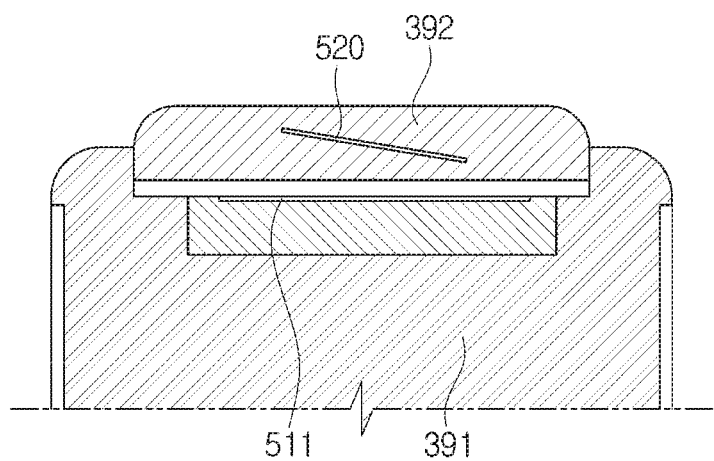
Figure 19D:
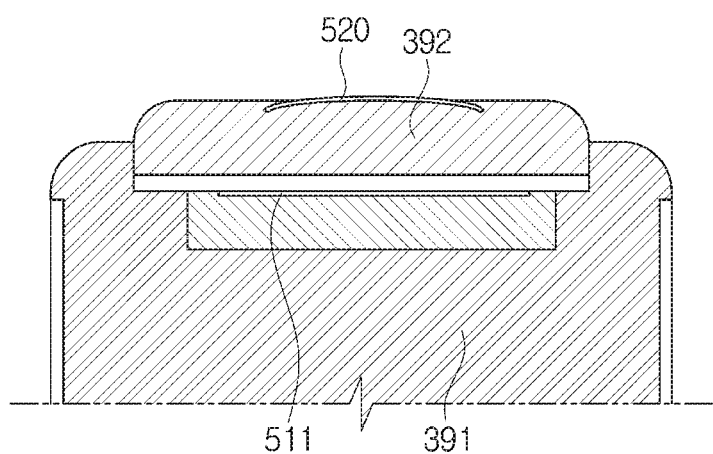
Figure 20:
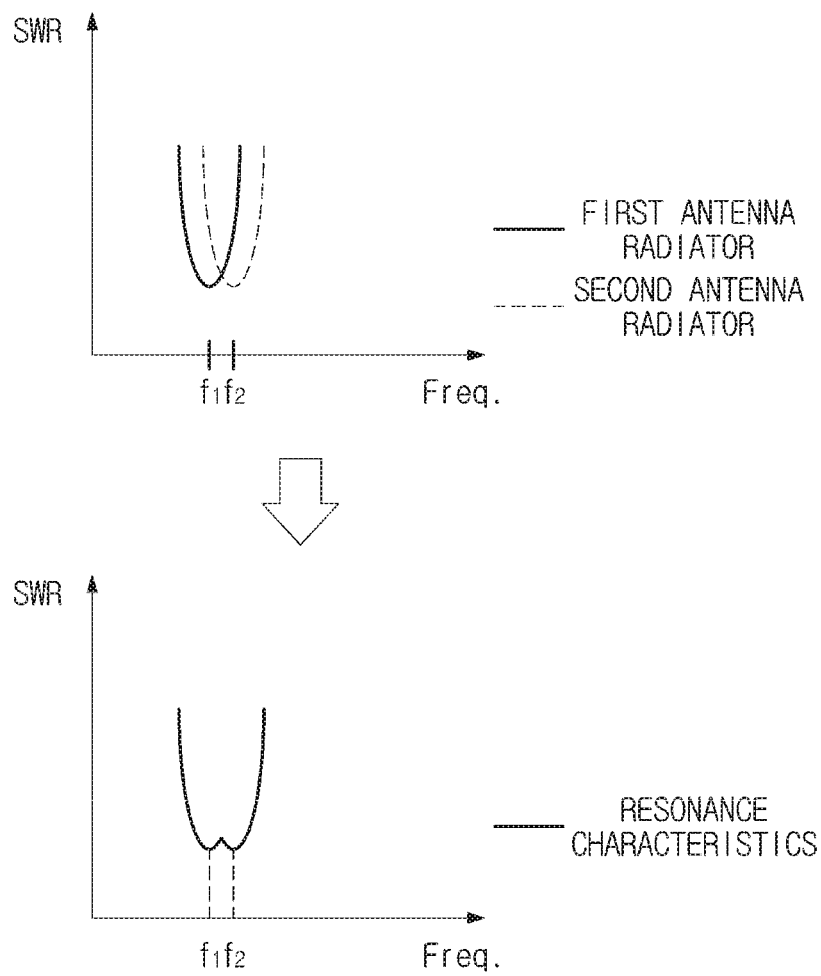
FIG. 20 is a graph illustrating resonance characteristics of a communication assembly of an X-ray detector in accordance with an exemplary embodiment.

FIG. 18 is a cross-sectional view taken along line A-A' of an X-ray detector 300 of FIG. 11 to illustrate a communication assembly of an X-ray detector in accordance with an exemplary embodiment, FIGS. 19A, 19B, 19C, and 19D are cross-sectional views illustrating various positions of position of antenna radiator, and FIG. 20 is a graph illustrating resonance characteristics of a communication assembly 500 of an X-ray detector 300 in accordance with an exemplary embodiment.

As illustrated in FIGS. 19 and 20, the communication assembly 500 wirelessly communicating with the workstation 170 may be provided in one side of the X-ray detector 300. Particularly, the communication assembly 500 may be disposed in the lateral member 390 of the X-ray detector 300.

The lateral member 390 may include a side frame 391 forming a lateral exterior, and a cover 392 coupled to the outside of the side frame 391 to protect the X-ray detector 300.

At least one coupling groove 391a may be formed in the side frame 391, and at least one coupling protrusion 392a having a shape corresponding to the coupling groove 391a of the side frame 391 may be formed in the cover 392. Accordingly, the coupling protrusion 392a of the cover 392 may be coupled to the coupling groove 391a of the side frame 391 so that the cover 392 may be fixed to the side frame 391, but the fixation method between the cover 392 and the side frame 391 is not limited thereto.

An accommodation groove 391b in which the first antenna radiator 510 is placed may be provided in the side frame 391. The accommodation groove 391b may have a shape corresponding to the shape of the first antenna radiator 510, and the surface of the accommodation groove 391b may be formed of electric insulation material, e.g. plastic. However, the accommodation groove 391b may be omitted according to the manufacture method of the first antenna radiator 510.

The cover 392 may coupled to the side frame 391. To protect the X-ray detector 300 from the external impact, the cover 392 may be formed of rubber, plastic, or reinforced plastic, but is not limited thereto.

Between the cover 392 and the side frame 391, a certain separation space 393 may be provided. By the certain separation space 393 between the cover 392 and the side frame 391, the first antenna radiator 510 and the second antenna radiator 520 may be spaced apart from each other with a certain distance.

The first antenna radiator 510 may be coupled to the side frame 391. The first antenna radiator 510 may be provided in a way of being coupled to the accommodation groove 391b of the lateral member 390, but the forming method of the first antenna radiator 510 is not limited thereto.

For example, the first antenna radiator 510 may be directly coupled to the side frame 391 by an adhesive member. In addition, the first antenna radiator 510 may be formed by the related art manufacturing method, e.g. Laser Direct Structuring (LDS), double injection, (Insert Mold Antenna (IMA), and FLEXIBLE PCB (FPCB) or by a manufacturing method that is to be developed in the future.

In this case, the LSD is a method of forming an antenna radiator in a manner to process thermoplastic resin through a laser and then plate the processed thermoplastic resin, the double injection is a method of forming an antenna radiator in a manner to perform a first injection molding and a second injection molding and then to plate them, and the IMA is a method of forming an antenna radiator in a manner to perform insertion of mold.

The second antenna radiator 520 may be formed in the cover 392. The second antenna radiator 520 may be disposed in an inner surface of the cover 392 to be spaced apart from the first antenna radiator 510. As mentioned above, when the second antenna radiator 520 is disposed in the inner surface of the cover 392, by the certain separation space 393 between the cover 392 and the side frame 391, the second antenna radiator 520 and the first antenna radiator 510 may be spaced apart from each other.

There is no limitation in the position of the second antenna radiator 520, but as mentioned above, at least one portion of the second antenna radiator 520 may be overlapped with the first antenna radiator 510. For example, the position of the second antenna radiator 520 may be determined to allow at least one portion thereof to be overlapped with the high frequency patch 511, as illustrated in FIG. 17.

The second antenna radiator 520 may be provided in the inner surface of the cover 392 by an adhesive member. In addition, the second antenna radiator 520 may be formed by the related art manufacturing method, e.g. Laser Direct Structuring (LDS), double injection, (Insert Mold Antenna (IMA), and FLEXIBLE PCB (FPCB) or by a manufacturing method that is to be developed in the future.

Meanwhile, FIGS. 17 and 18 illustrate that the second antenna radiator 520 is coupled to the inner side of the cover 392, but the position of the second antenna radiator 520 is not limited thereto.

For example, as illustrated in FIG. 19A, the second antenna radiator 520 may be disposed in an outer surface of the cover 392. As mentioned above, when the second antenna radiator 520 is disposed in the outer surface of the cover 392, the cover 392 may formed in the form of the symbol of the manufacturer.

For another example, as illustrated in FIGS. 19B and 19C, the second antenna radiator 520 may be mounted to the inside of the cover 392. In this case, the second antenna radiator 520 may be mounted to be parallel with the high frequency patch 511, as illustrated in FIG. 19B or the second antenna radiator 520 may be mounted to have a certain angle with the high frequency patch 511, as illustrated in FIG. 19C.

For another example, the second antenna radiator 520 may be disposed so that one portion thereof is mounted to the inside of the cover 392, as illustrated in FIG. 19D.

As illustrated in FIG. 19, when the second antenna radiator 520 is disposed in a position other than the inner surface of the cover 392, the second antenna radiator 520 may be spaced apart from the first antenna radiator 510 by the cover 392 with a certain distance and thus a width of the certain separation space 393 between the cover 392 and the side frame 391 may be reduced or may be omitted.

In other words, when the second antenna radiator 520 is disposed on the inside or the outer surface of the cover 392 other than the inner surface of the cover 392, the cover 392 may be coupled to the side frame 391 without a space.

As mentioned above, when the first antenna radiator 510 and the second antenna radiator 520 are spaced apart from each other, the second antenna radiator 520 may resonate with the first antenna radiator 510 so that the transmission performance of the communication assembly 500 may be improved, as illustrated in FIG. 20.

As illustrated in FIG. 20, the high frequency patch 511 of the first antenna radiator 510 may have radiation characteristics having a center frequency f1 and the second antenna radiator 520 fed by the high frequency patch 511 may have radiation characteristics having a center frequency f2. Therefore, radiation characteristics of W shape may be showed by the resonance of the second antenna radiator 520 and the first antenna radiator 510. That is, due to the resonance of the second antenna radiator 520 and the first antenna radiator 510, a bandwidth of the first antenna radiator 510 may be wide so that the communication assembly 500 may have wide band characteristics.

In addition, since the reflection loss of the first antenna radiator 510 is reduced due to the resonance of the second antenna radiator 520, the overall communication performance may be improved.

Figure 21:
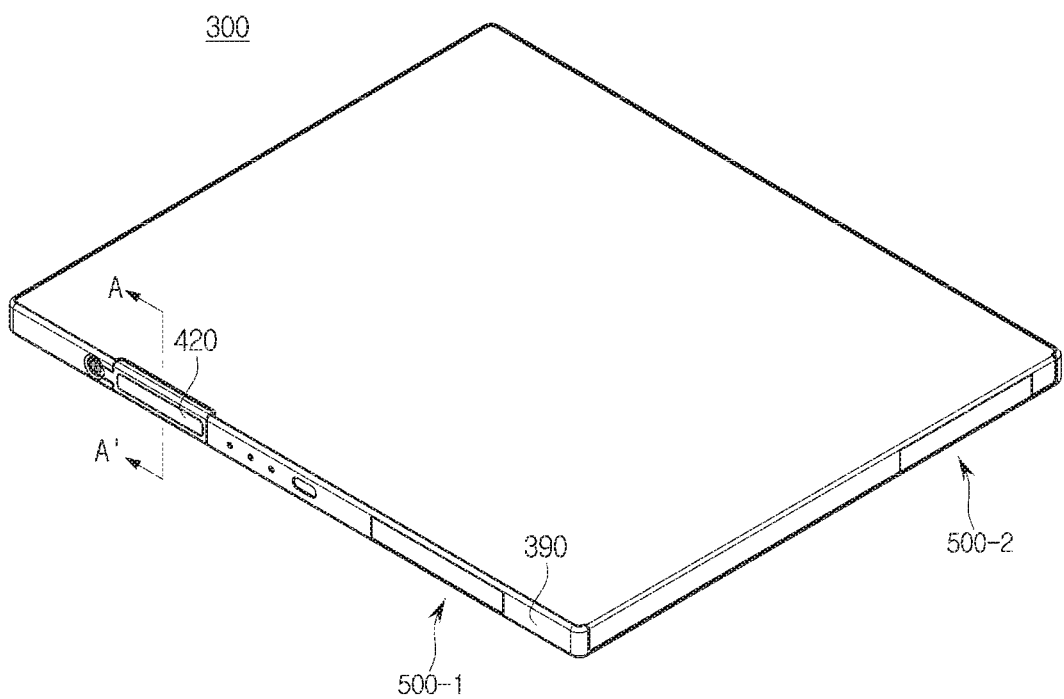
FIG. 21 is a perspective view illustrating an X-ray detector in accordance with an exemplary embodiment.

FIG. 21 is a perspective view illustrating an X-ray detector 300 in accordance with an exemplary embodiment.

As illustrated in FIG. 21, an X-ray detector 300 in accordance with an exemplary embodiment may include a plurality of communication assemblies 500. The X-ray detector 300 may perform a wireless communication by Multiple Input Multiple Output (MIMO) method by using the plurality of communication assemblies 500.

To perform the communication by Multiple Input Multiple Output (MIMO) method, the plurality of communication assemblies 500 may be disposed with a certain angle. For example, the first communication assembly 500-1 may be disposed on a first lateral surface, and a second communication assembly 500-2 may be disposed on a second lateral surface perpendicular to the first lateral surface.

Figure 22:
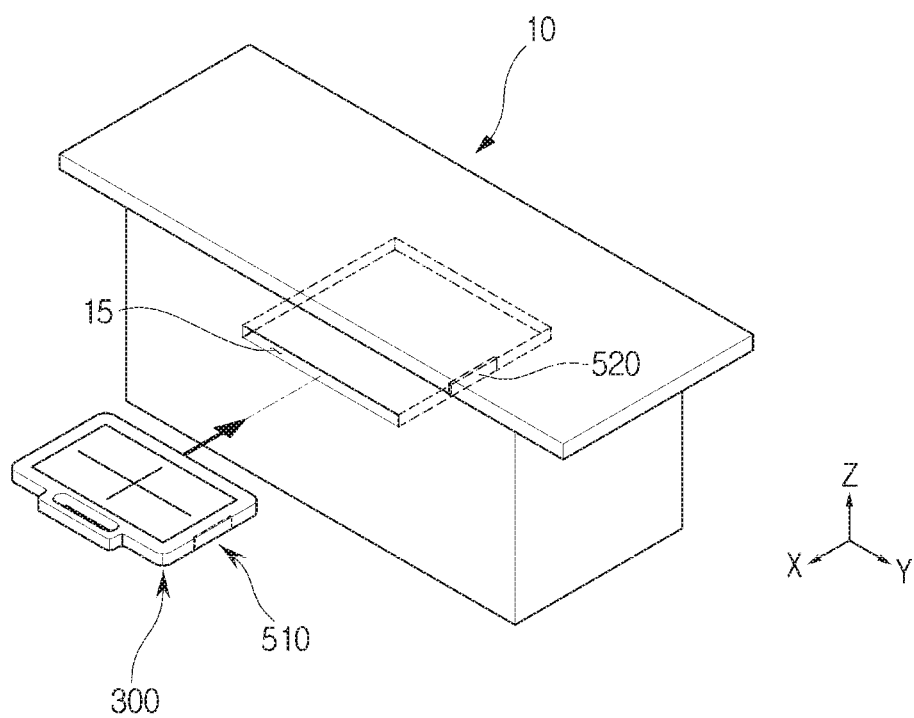
FIGS. 22 and 23 are views illustrating an X-ray detector in accordance with an exemplary embodiment.
Figure 23:
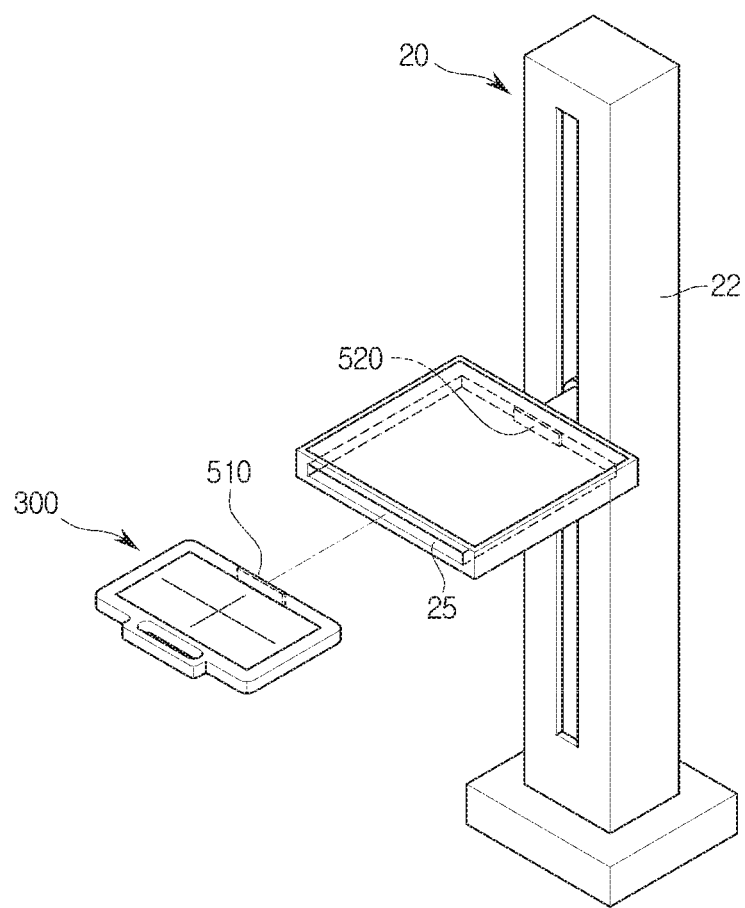

FIGS. 22 and 23 are views illustrating an X-ray detector 300 in accordance with an exemplary embodiment.

Referring to FIGS. 22 and 23, the second antenna radiator 520 may be disposed on the X-ray detector 300, but the second antenna radiator 520 may be disposed in the accommodation portions 15 and 25.

As mentioned above, the X-ray detector 300 may be inserted into the accommodation portions 15 and 25. Therefore, the second antenna radiator 520 provided in the accommodation portions 15 and 25 may resonate with the first antenna radiator 510 provided in the X-ray detector 300 so that the wireless communication performance of the first antenna radiator 510 may be improved.

Particularly, the second antenna radiator 520 may be disposed on a position corresponding to the first antenna radiator 510. As mentioned above, the first antenna radiator 510 may be provided in the side frame 391 so that the second antenna radiator 520 and the first antenna radiator 510 may be spaced apart from each other with a certain distance by the cover 392.

The second antenna radiator 520 provided in the accommodation portions 15 and 25 may be indirect proximity by the first antenna radiator 510 provided in the X-ray detector 300 so that the wireless communication efficiency of the first antenna radiator 510 may be improved.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray detector comprising:
   a side frame;
   a first antenna radiator supplied with a power by being coupled to the side frame and having a first surface extending in a lengthwise dimension of the first antenna radiator;
   a cover configured to be coupled to an outside of the side frame, for covering the first antenna radiator; and
   a second antenna radiator provided in the cover opposing the first antenna radiator and configured to resonate with the first antenna radiator, the second antenna radiator having a second surface extending in the lengthwise dimension and facing the first surface of the first antenna radiator, the second surface of the second antenna radiator being spaced apart from the first surface of the first antenna radiator with a free space interposed therebetween.

2. The X-ray detector of claim 1, wherein the second antenna radiator is disposed in the cover, and
   at least a portion of the second antenna radiator overlaps the first antenna radiator disposed in the side frame, in the lengthwise dimension.

3. The X-ray detector of claim 1, wherein the cover comprises an inner surface facing the first antenna radiator and an outer surface opposing the inner surface, and
   the second antenna radiator is disposed in the inner surface or the outer surface of the cover.

4. The X-ray detector of claim 1, wherein
   the second antenna radiator is mounted to the cover.

5. The X-ray detector of claim 1, wherein the second antenna radiator has a certain shape to resonate with the first antenna radiator.

6. The X-ray detector of claim 1, wherein the first antenna radiator comprises:
   a high frequency patch configured to radiate electromagnetic waves of a first frequency; and
   a low frequency patch configured to radiate electromagnetic waves of a second frequency and disposed in a row with respect to the high frequency patch, in the lengthwise dimension.

7. The X-ray detector of claim 6, wherein the second antenna radiator overlaps the high frequency patch, in the lengthwise dimension.

8. The X-ray detector of claim 6, wherein the first frequency is a WiFi communication frequency, and
   the second frequency is a Bluetooth communication frequency.

9. The X-ray detector of claim 6, further comprising:
   a connection member configured to electrically connect the high frequency patch to the low frequency patch.

10. The X-ray detector of claim 1, further comprising:
    a power supply configured to supply the power to the first antenna radiator, by transmitting electromagnetic waves energy to the first antenna radiator.

11. The X-ray detector of claim 10, wherein the second antenna radiator is supplied with the power indirectly, through the first antenna radiator.

12. The X-ray detector of claim 1, wherein an entirety of the second surface of the second antenna radiator faces an entirety of the first surface of the first antenna radiator.

13. An X-ray imaging apparatus comprising:
    an X-ray detector provided with a first antenna radiator for a wireless communication, the first antenna radiator having a first surface extending in a lengthwise dimension of the first antenna radiator; and
    an accommodation portion which accommodates the X-ray detector and is provided with a second antenna radiator opposing the first antenna radiator and configured to resonate with the first antenna radiator, the second antenna radiator having a second surface extending in the lengthwise dimension and facing the first surface of the first antenna radiator, the second surface of the second antenna radiator being spaced apart from the first surface of the first antenna radiator with a free space interposed therebetween, wherein the second antenna radiator has a shape to resonate with the first antenna radiator.

14. The X-ray imaging apparatus of claim 13, wherein at least a portion of the second antenna radiator overlaps the first antenna radiator, in the lengthwise dimension.

15. The X-ray imaging apparatus of claim 13, further comprising:
a power supply configured to supply a power to the first antenna radiator,
wherein the second antenna radiator is supplied with the power indirectly, through the first antenna radiator.

16. The X-ray imaging apparatus of claim 13, wherein the first antenna radiator comprises:
a high frequency patch configured to radiate electromagnetic waves of a first frequency; and
a low frequency patch configured to radiate electromagnetic waves of a second frequency and disposed in a row with respect to the high frequency patch, in the lengthwise dimension.

17. The X-ray imaging apparatus of claim 16, wherein the first frequency is a WiFi communication frequency, and
the second frequency is a Bluetooth communication frequency.

18. The X-ray imaging apparatus of claim 13, wherein the X-ray detector comprises a plurality of communication assemblies including a plurality of first antenna radiators and a plurality of second antenna radiators,
each pair of one among the plurality of first antenna radiators and one among the plurality of second antenna radiators form one of the plurality of communication assemblies, and
the plurality of communication assemblies is configured to communicate with an outside by Multiple Input Multiple Output (MIMO) method,
the first antenna radiator is included into the plurality of first antenna radiators, and
the second antenna radiator is included into the plurality of second antenna radiators.

* * * * *